(12) United States Patent
Bydder et al.

(10) Patent No.: US 9,759,794 B2
(45) Date of Patent: Sep. 12, 2017

(54) MRI-BASED FAT DOUBLE BOND MAPPING

(75) Inventors: Mark Bydder, San Diego, CA (US);
Gavin Hamilton, San Diego, CA (US);
Michael Middleton, San Diego, CA (US); Claude Sirlin, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 949 days.

(21) Appl. No.: 13/883,273

(22) PCT Filed: Nov. 7, 2011

(86) PCT No.: PCT/US2011/059660
§ 371 (c)(1),
(2), (4) Date: Dec. 16, 2013

(87) PCT Pub. No.: WO2012/061839
PCT Pub. Date: May 10, 2012

(65) Prior Publication Data
US 2015/0309137 A1 Oct. 29, 2015

Related U.S. Application Data

(60) Provisional application No. 61/410,664, filed on Nov. 5, 2010.

(51) Int. Cl.
*G01N 24/00* (2006.01)
*G01N 31/00* (2006.01)
(Continued)

(52) U.S. Cl.
CPC .......... *G01R 33/4828* (2013.01); *A61B 5/055* (2013.01); *G01R 33/34* (2013.01); *G01R 33/54* (2013.01)

(58) Field of Classification Search
CPC .............. A61K 35/35; A61K 49/0082; A61K 49/1809; A61B 5/055; A61B 5/4872;
(Continued)

(56) References Cited

U.S. PATENT DOCUMENTS 7,468,605 B2 * 12/2008 Yu ................. G01N 24/08
324/307
2008/0081375 A1 * 4/2008 Tesiram ........... G01N 24/08
436/57

(Continued)

OTHER PUBLICATIONS

Tonkelaar et al., "Body fat distribution in relation to breast cancer in women participating in the DOM-project", Breast Cancer Research and Treatment, 1995, v. 34, pp. 55-61.*
(Continued)

*Primary Examiner* — Yelena G Gakh
(74) *Attorney, Agent, or Firm* — Perkins Coie LLP

(57) ABSTRACT

Techniques, apparatus and systems are described for using parameters including chain length, number of double bonds and number of double-double bonds of a complex, magnetic resonance imaging (MRI)-generated fat spectrum to determine the composition and properties of fat and to perform various diagnostic functions. In one aspect, a method using MRI to characterize fat includes acquiring a magnetic resonance (MR) image that includes MR data from a target, determining fat characterization parameters based on the acquired MR data, and using the determined fat characterization parameters to produce a relationship between regions of fat and/or water in the MR image.

25 Claims, 11 Drawing Sheets

(51) Int. Cl.
*G01R 33/48* (2006.01)
*A61B 5/055* (2006.01)
*G01R 33/34* (2006.01)
*G01R 33/54* (2006.01)

(58) Field of Classification Search
CPC ....... A61B 5/7257; A61B 6/482; A61B 6/032; A61B 5/4869; A61B 6/583; A61B 5/0537; A61B 2576/00; A61B 5/0035; A61B 5/004; A61B 5/01
See application file for complete search history.

(56) References Cited

U.S. PATENT DOCUMENTS

2009/0276187 A1* 11/2009 Martin ................... G01N 24/08 702/189
2010/0156413 A1   6/2010 Chen et al.

OTHER PUBLICATIONS

"Does body weight affect cancer risk?", American Cancer Society, Feb. 5, 2015 http://www.cancer.org/cancer/cancercauses/dietandphysicalactivity/bodyweightandcancerrisk/body-weight-and-cancer-risk-effects, pp. 1-2.*
Hernando et al., "Chemical Shift-Based Water/Fat Separation: A Comparison of Signal Models", Magn. Reson. Med., published on-line Jun. 30, 2010, v. 64, pp. 811-822.*
An, Xiang, "Chemical Shift Imaging With Spectrum Modeling," Magn. Reson Med 2001; 46: pp. 126-130.
Araya J et al. "Increase in long-chain polyunsaturated fatty acid n-6/n-3 ratio in relation to hepatic steatosis in patients with non-alcoholic fatty liver disease," Clin Sci (Lond) 2004;106: pp. 635-643.
Bydder M. et al. "Relaxation effects in the quantification of fat using gradient echo imaging,.". Magn Reson Imaging. Apr. 2008;26(3): pp. 347-359.
Griffitts J et al., "In vivo MRS assessment of altered fatty acyl unsaturation in liver tumor formation of a TFG α/c-myc transgenic mouse model," J Lipid Res 2009; 50: pp. 611-622.
Hu FB et al. "Optimal diets for prevention of coronary heart disease," J. Am. Med. Assoc, Nov. 27, 2002; 288, pp. 2569-2578.
Manco M et al., "Insulin resistance directly correlates with increased saturated fatty acids in skeletal muscle triglycerides," Metabolism 2000; 49: pp. 220-224.
Pezeshakian, Noori et al. "Fatty Acid Composition of Epicardial and Subcutaneous Human Adipose Tissue," Metabolic Syndrome and Related Disorders, vol. 7, No. 2, 2009, pp. 125-132.
Ren J. et al. "Composition of adipose tissue and marrow fat in humans by 1H NMR at 7 Tesla," J Lipid Res 2008;49: pp. 2055-2062.
Risérus U. et al. "Dietary fats and prevention of type 2 diabetes," Prog Lipid Res 2009; 48: pp. 44-51.
Simonsen, N. et al. "Adipose tissue omega-3 and omega-6 fatty acid content and breast cancer in the EURAMIC study," Am. J. Epidemoil, 1998; 146: pp. 342-352.
Storlien LH et al. "Diet composition and insulin action in animal models," British Journal of Nutrition, 2000; 83 Suppl 1: S85-S90.
Victor TA et al. "Detecting fatty acids of dietary origin in normal and cancerous human breast tissue by 13C nuclear magnetic resonance spectroscopy," Br J Cancer 1993;68: pp. 336-341.
Yu H, Shimakawa A, McKenzie CA, Brodsky E, Brittain JH, Reeder SB. Multiecho water-fat separation and simultaneous R2* estimation with multifrequency fat spectrum modeling. Magn Reson Med. 2008; 60: pp. 1122-1134.
International Search Report and Written Opinion of International Application No. PCT/US2011/059660; Date of Mailing: May 29, 2012; 7 pages.

* cited by examiner

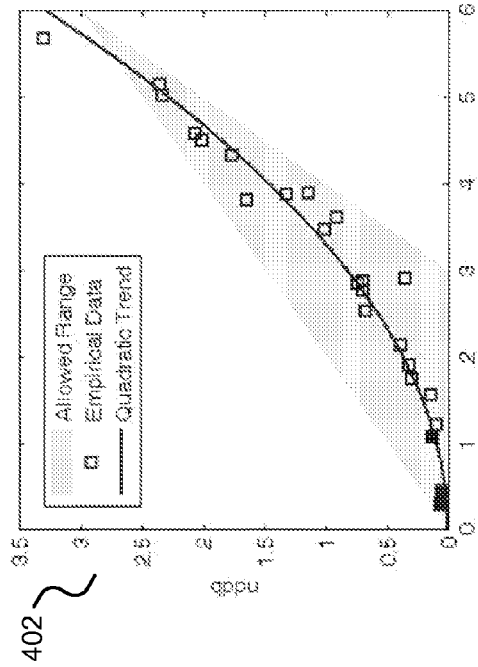
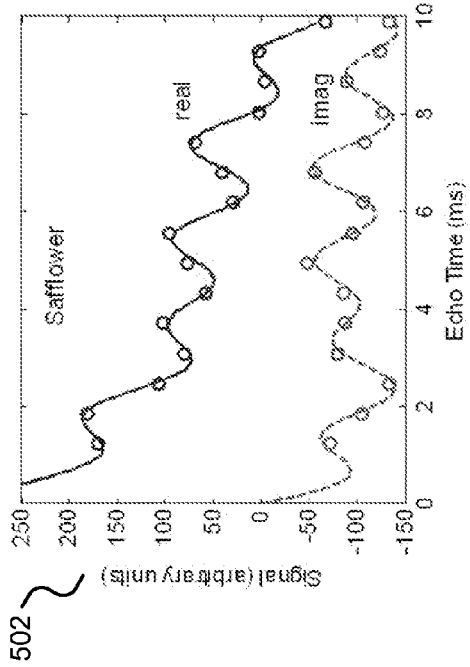
FIG. 4A
FIG. 4B
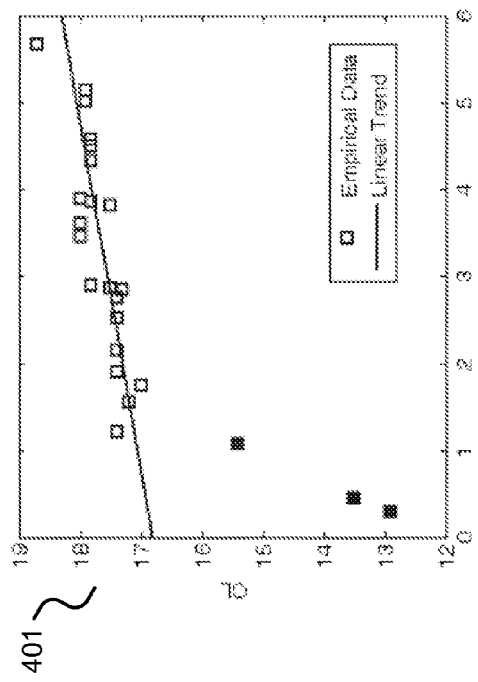
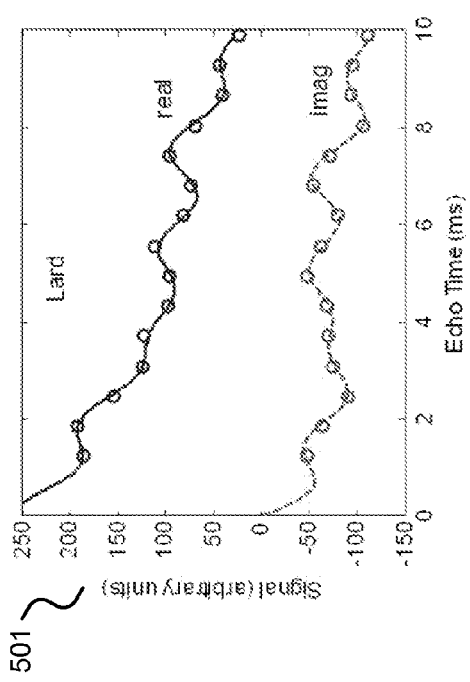
FIG. 5A
FIG. 5B

MRI-BASED FAT DOUBLE BOND MAPPING

CROSS-REFERENCE TO RELATED APPLICATION

This patent document claims priority of U.S. Provisional Patent Application No. 61/410,664, filed Nov. 5, 2010, entitled "MRI-BASED FAT DOUBLE BOND MAPPING", the entire disclosure of which is incorporated herein by reference for all purposes.

FEDERALLY SPONSORED RESEARCH OR DEVELOPMENT

The invention was made with government support under Grant No. R01 #DK075128 awarded by the National Institutes of Health (NIH). The government has certain rights in the invention.

BACKGROUND

This patent document relates to magnetic resonance imaging (MRI) technologies.

MRI is a medical imaging technique used for imaging internal biological structures based on the property of nuclear magnetic resonance (NMR). NMR is a physical property in which the nuclei of atoms absorb and re-emit electromagnetic energy at a specific resonance frequency in the presence of a magnetic field. The absorption and reemission of energy can be dependent on the strength of the magnetic field and the magnetic property of the atoms (e.g., atoms whose nuclei possesses magnetic spin). For example, the different nuclei in a molecule absorb the electromagnetic energy by the magnetic field at slightly different frequencies, e.g., a shift from a reference resonance frequency. This shift can be represented as a field-independent dimensionless value known as the chemical shift. The chemical shift can be quite small (e.g., $\sim 10^{-6}$) and can be reported as ratio in parts per million (ppm), e.g., $10^6 \cdot$(measured frequency−reference frequency)/reference frequency.

NMR can be used to determine physical and chemical properties of atoms or molecules such as structure, dynamics, reaction state, and chemical environment of molecules. NMR spectroscopy, also referred to as magnetic resonance (MR) spectroscopy, can be used to obtain high spectral resolution data on organic molecules. For example, MR spectroscopy can be used to obtain high spectral resolution data of fat, but with poor spatial resolution. It is also difficult to analyze the data from MR spectroscopy.

SUMMARY

The systems, processes, apparatuses and materials described in this patent document can used to implement MR imaging using parameters of a complex, MRI-generated fat spectrum to model the composition and properties of fat. Implementations of the disclosed technology can be used to perform various diagnostic and treatment plans.

In one aspect of the disclosed technology, a method for using MRI to characterize fat includes acquiring an MR image that includes MR data from a target, determining fat characterization parameters based on the acquired MR data, and using the determined fat characterization parameters to produce a relationship between regions of fat, regions of water, or regions of fat and water in the MR image.

Various implementations of the above aspect can include one or more of the following features. The method can include determining fat characterization parameters by selecting initial values of the fat characterization parameters, estimating values of the fat characterization parameters by iteratively minimizing error between the fat characterization parameters and the acquired MR data, generating an MR signal by simulation using the estimated values of the fat characterization parameters, and matching the simulated MR signal with an actual MR signal based on the acquired MR data. The fat characterization parameters can include an amount of fat, an amount of water, an initial phase, a field inhomogeneity, a T2*, and at least one fat spectrum parameter. The fat spectrum parameter can include a number of double bonds (NDB), a number of double-double bonds (NDDB), and a chain length (CL) of a biochemical. The method can include determining CL from NDB by a linear approximation. The linear approximation can be substantially $CL=16.8+0.24 \cdot NDB$. The method can include determining NDDB from NDB by a non-linear approximation. The non-linear approximation can be substantially $NDDB=0.092 \cdot NDB^2$. The method can include the amount of water and the amount of fat being estimated by selecting an initial phase of water and an initial phase of fat to be equal at an echo-time of zero. The method can include producing the relationship that further includes regions of triglycerides. The method can include producing the relationship that further includes a number of double bonds. The determined fat characterization parameters can describe a composition of fat in the target. The composition of fat can include at least six known peak areas, whereby peak area 1 and peak area 2 can be determined based on the peak area 3, the peak area 4, the peak area 5, and the peak area 6. The method can further include using the relationship to assess a patient's status with regard to a disease that includes cancer, type 2 diabetes, heart disease, liver disease, and nonalcoholic steatohepatitis (NASH).

In another aspect, an MRI system to characterize fat includes an MRI machine that acquires at least one MR image from a target and a processing unit configured to command the MRI machine to acquire at least one MR image that includes MR data from the target, determine fat characterization parameters based on the acquired MR data, and use the determined fat characterization parameters to produce a relationship between regions of fat, regions of water, or regions of fat and water in the MR image.

Various implementations of the above aspect can include one or more of the following features. The processing unit of the MRI system can be configured to determine the fat characterization parameters by selecting initial values of the fat characterization parameters, estimating values of the fat characterization parameters by iteratively minimizing error between the fat characterization parameters and the acquired MR data, generating an MR signal by simulation using the estimated values of the fat characterization parameters, and matching the simulated MR signal with an actual MR signal based on the acquired MR data. The fat characterization parameters can include an amount of fat, an amount of water, an initial phase, a field inhomogeneity, a T2*, and at least one fat spectrum parameter. The fat spectrum parameter can include an NDB, an NDDB, and a CL of a biochemical. The processing unit of the MRI system can be configured to perform using the relationship to assess a patient's status with regard to a disease that includes cancer, type 2 diabetes, heart disease, liver disease, and NASH.

In another aspect, a computer program product comprising a nonvolatile computer-readable storage medium having instructions stored thereon includes code for acquiring an MR image that includes MR data from a target, code for determining fat characterization parameters based on the acquired MR data, and code for using the determined fat characterization parameters to produce a relationship between regions of fat, regions of water, or regions of fat and water in the MR image.

Various implementations of the above aspect can include one or more of the following features. The code for determining fat characterization parameters can include code for selecting initial values of fat characterization parameters, code for estimating values of the fat characterization parameters by iteratively minimizing error between the fat characterization parameters and the acquired MR data, code for generating an MR signal by simulation using the estimated values of the fat characterization parameters, and code for matching the simulated MR signal with an actual MR signal based on the acquired MR data. The nonvolatile computer-readable storage medium can further include code for using the relationship to assess a patient's status with regard to a disease that includes at least one of cancer, type 2 diabetes, heart disease, liver disease, and NASH.

In another aspect, an MRI method includes modeling a MRI-generated fat spectrum from an MR image of a target using at least one of three parameters including a chain length, a number of double bonds, or a number of double bonds.

Various implementations of the above aspect can include one or more of the following features. The modeling of the MRI method can include measuring a number of double bonds based on the MR image. The modeling of the MRI method can include determining fat characterization parameters based on the MR image and using the determined fat characterization parameters to produce a relationship between regions of fat, regions of water, or regions of fat and water in the MR image. The MRI method can further include using the relationship to characterize composition of fat, quantity of fat, localization of fat, and change in spatial distribution of fat.

The disclosed technology can provide one or more of the following advantages. For example, the described techniques, apparatus and systems can be used to determine the type and saturation level of fat, which can be used in diagnosis and treatment plans for disease, such as (1) cancer to evaluate tumors/lesions and decide if they are malignant or benign, (2) liver disease to differentiate between simple steatosis and steaohepatitis, and (3) diabetes to detect brown fat, which is an indicator for predisposition to develop diabetes. The disclosed technology can be used to determine regional differences in fat composition throughout the body, which can suggest depot specific impact of stored fatty acids on adipocyte function and metabolism. Additionally, the disclosed technology can be used to determine the composition of triglycerides present, which can indicate the risk of many disorders, including cancer, type 2 diabetes, heart disease and nonalcoholic steatohepatitis (NASH).

BRIEF DESCRIPTION OF THE DRAWINGS

FIGS. 4A and 4B show exemplary plots of the chain length (CL) and the number of double-double bonds (NDDB) as a function of the number of double bonds (NDB) in various oils and fats.

FIGS. 5A and 5B show exemplary plots of curve fitted data for lard and safflower oil.

Like reference symbols and designations in the various drawings indicate like elements.

DETAILED DESCRIPTION

The systems, processes, apparatuses and materials described in this patent document can used to implement MR imaging using parameters of a complex, MRI-generated fat spectrum to model the composition and properties of fat. Implementations of the disclosed technology can be used to perform various diagnostic and treatment plans.

In one aspect, an exemplary MRI system of the disclosed technology can be used to characterize the properties of fat within the volume and/or section of a desired target (e.g., in a subject, such as a human patient) from an MR image in a manner that can determine particular biochemical parameters (that can include chain length (CL), number of double bonds (NDB), and number of double-double bonds (NDDB)) to generate a complete fat characterization profile. For example, the exemplary MRI system can be used to interrogate fat depots, in which fat profiles are determined from an MR image despite relatively limited spectral information in a set of MR images as compared to MR spectra derived from MR spectroscopy characterization modalities. For example, in MR spectroscopy, thousands of acquired data points would be required to represent an MR spectrum that could be used to characterize the fat profile within one voxel of a desired target in a subject. Using MR spectroscopy techniques, a complete fat characterization profile would have to be determined one voxel (e.g., 1 cm$^2$ of the target region from the subject) at a time. Furthermore, for example, in subjects with small amounts of fat or where the fat occurs in thin layers or at boundaries, imaging can provide definitive voxel localization and the spatial distributional change in type of fat in the body. The exemplary MRI system can characterize the properties of fat and generate a complete fat characterization profile of a subject across the entire volume of an acquired MR image by employing the exemplary parameters of CL, NDB, and/or NDDB.

Implementation of systems, methods, and devices of the disclosed technology can provide the desired, clinically-relevant information about fat content so that there is no need to perform MR spectroscopy. The disclosed technology can include an exemplary model to characterize fat properties of an MR spectrum in terms of, for example, the three biochemical parameters of CL, NDB, and NDDB, which can allow MRI imaging without spectroscopy. Existing MRI scans and techniques may provide sufficient spatial information, but insufficient spectral information. On the other hand, for example, fat characterization can be performed by implementing the model using at least one of three biochemical parameters that can be extracted from data points existent in a set of acquired MR images, which can characterize fat properties from the entire volume of tissue sampled, rather than acquire a spectrum from a single voxel (as acquiring from every voxel of the entire tissue sample would be impractical).

Figure 1:
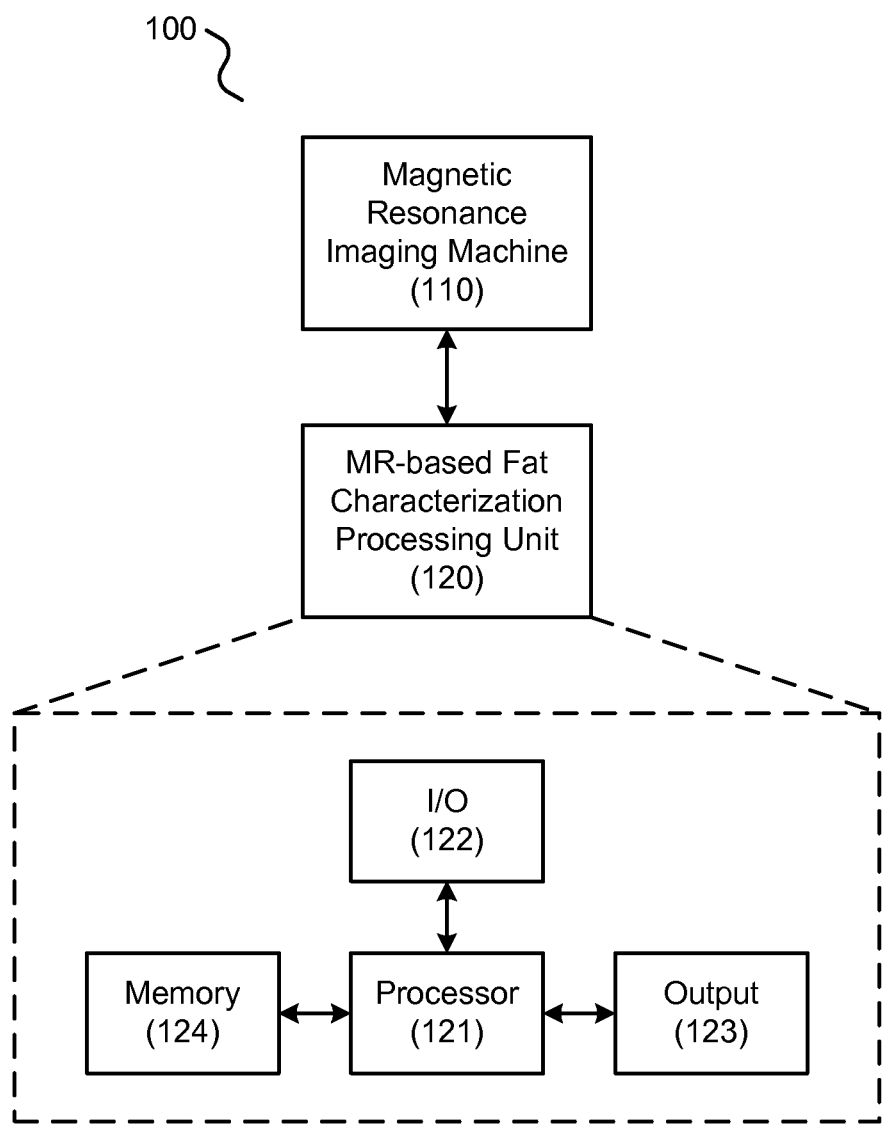
FIG. 1 shows an exemplary MR-based fat characterization system.

FIG. 1 shows an exemplary MR-based fat characterization system (100) for providing a complete description of the composition and properties of fat from a subject by using acquired MRI images that can be processed using a reduced parameter set that can include CL, NDB, and NDDB. FIG. 1 shows one aspect of the exemplary system (100) that can include a magnetic resonance imaging (MRI) machine (110), which can be controlled by a MR-based fat characterization processing unit (120).

The exemplary MRI machine (110) can be used in the system (100) to implement a MR-based fat characterization process under the control of the exemplary MR-based fat characterization processing unit (120). MRI machine (110) can include various types of MRI systems, which can perform at least one of a multitude of MRI scans that can include, but are not limited to, T1-weighted MRI scans, T2-weighted MRI scans, T2*-weighted MRI scans, spin (proton) density weighted MRI scans, diffusion tensor (DT) and diffusion weighted imaging (DWI) MRI scans, T1ρ MRI scans, magnetization transfer (MT) MRI scans, among others.

The exemplary MR-based fat characterization processing unit (120) can include a processor (121) that can be in communication with an input/output (I/O) unit (122), an output unit (123), and a memory unit (124). MR-based fat characterization processing unit (120) can be implemented as one of various data processing systems, such as a personal computer (PC), laptop, tablet, and mobile communication device. To support various functions of MR-based fat characterization processing unit (120), the exemplary processor (121) can be included to interface with and control operations of other components of MR-based fat characterization processing unit (120), such as the exemplary I/O unit (122), the exemplary output unit (123), and the exemplary memory unit (124).

To support various functions of the MR-based fat characterization processing unit (120), memory unit (124) can store other information and data, such as instructions, software, values, images, and other data processed or referenced by processor (121). Various types of Random Access Memory (RAM) devices, Read Only Memory (ROM) devices, Flash Memory devices, and other suitable storage media can be used to implement storage functions of memory unit (124). The exemplary memory unit (124) can store MRI data and information, which can include subject MRI image data including spatial and spectral data, MRI machine system parameters, data processing parameters (e.g., estimation variables including amount of fat, amount of water, initial phase, phase constraint parameters, type of fat, T2*, etc.), and processed parameters and data that can be used in the implementation of a MR-based fat characterization. Memory unit (124) can store data and information that can be used to implement a MR-based fat characterization process and that can be generated from a MR-based fat characterization algorithm and/or model.

To support various functions of the MR-based fat characterization processing unit (120), the exemplary I/O unit (122) can be connected to an external interface, source of data storage, or display device. Various types of wired or wireless interfaces compatible with typical data communication standards, such as Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement I/O unit (122). I/O unit (122) can interface with an external interface, source of data storage, or display device to retrieve and transfer data and information that can be processed by the processor (121), stored in the memory unit (124), or exhibited on the output unit (123).

To support various functions of the MR-based fat characterization processing unit (120), the output unit (123) can be used to exhibit data implemented by the exemplary MR-based fat characterization processing unit (120). The output unit (123) can include various types of display, speaker, or printing interfaces to implement the exemplary output unit (123). For example, the output unit (123) can include cathode ray tube (CRT), light emitting diode (LED), or liquid crystal display (LCD) monitor or screen as a visual display to implement the output unit (123). In other examples, the output unit (123) can include toner, liquid inkjet, solid ink, dye sublimation, inkless (such as thermal or UV) printing apparatuses to implement the output unit (123); the output unit (123) can include various types of audio signal transducer apparatuses to implement the output unit (123). The output unit (123) can exhibit data and information, such as patient diagnostic data, MRI machine system information, partially processed MR-based fat characterization processing information, and completely processed MR-based fat characterization processing information, among other types and forms of data and information. The output unit (123) can store data and information used to implement a MR-based fat characterization process and from an implemented MR-based fat characterization process.

Figure 2A:
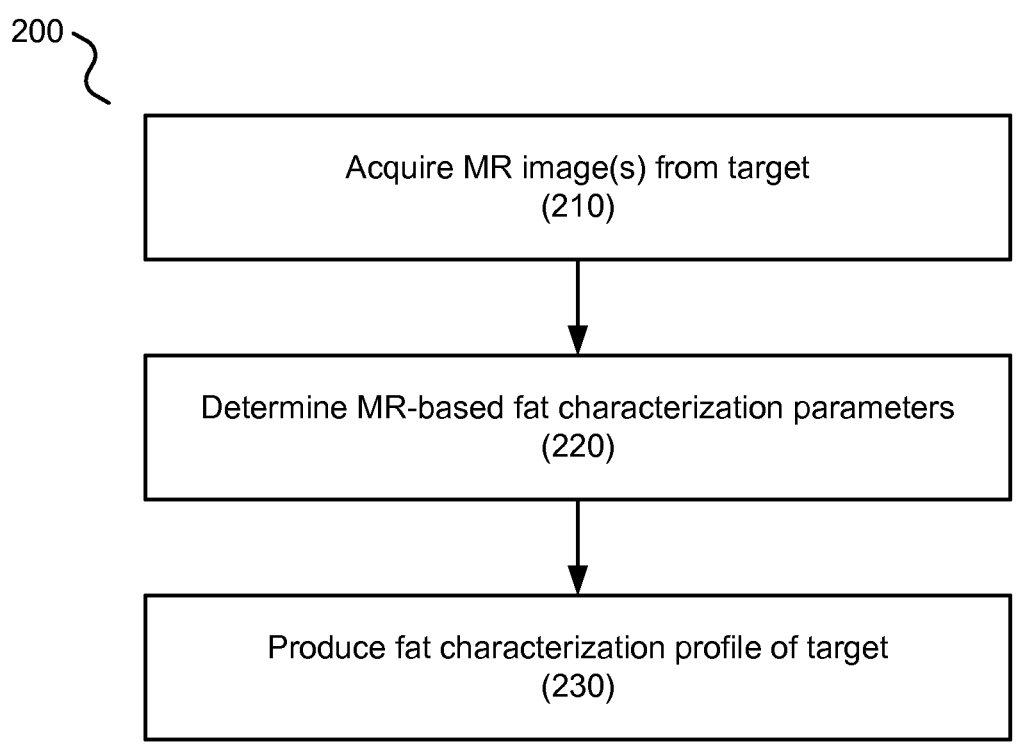
FIGS. 2A and 2B show diagrams of an exemplary method to produce a fat characterization profile from an acquired MRI image.
Figure 2B:
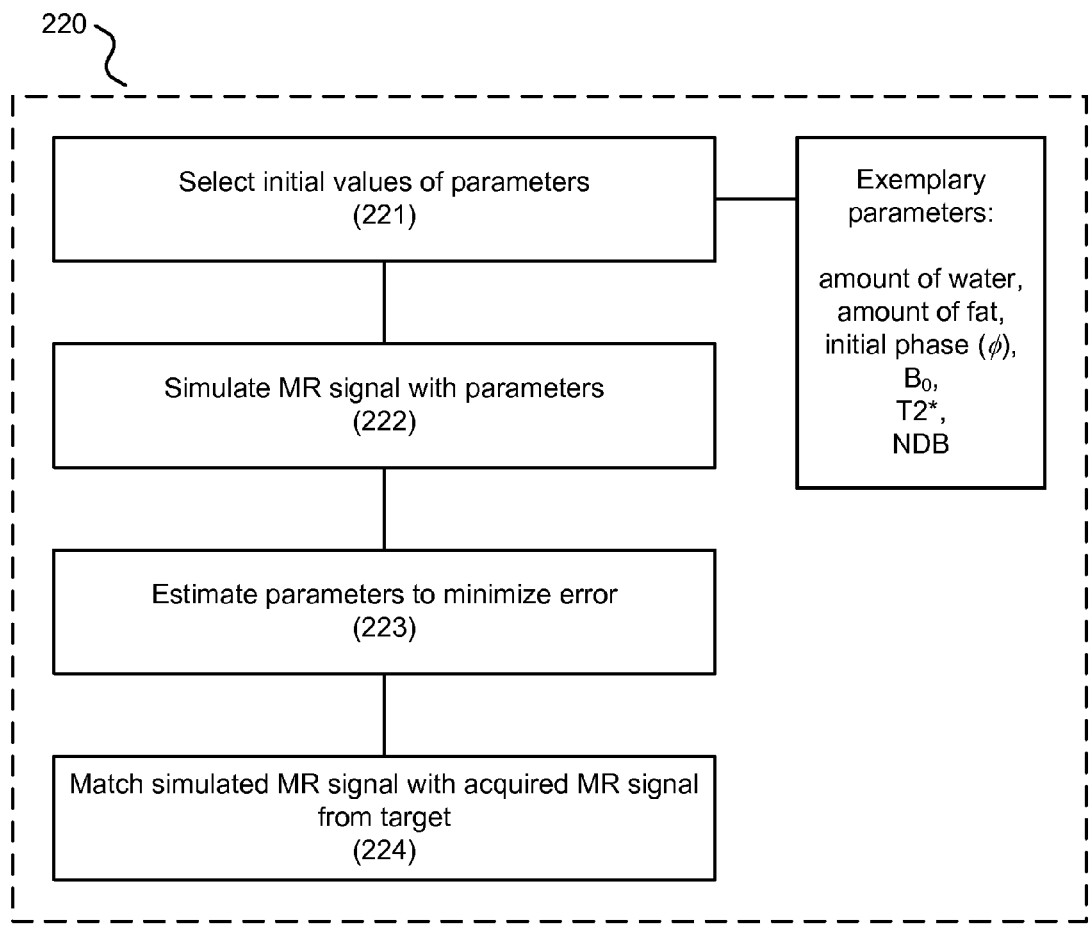

FIGS. 2A and 2B show process flow diagrams that describe implementation of an exemplary MRI method to produce a fat characterization profile from an acquired MRI image. Exemplary methods to characterize fat properties using MRI techniques can be performed on systems and devices, such as the exemplary system (100) illustrated in FIG. 1. For example, FIG. 2A shows an exemplary method (200) that includes a process (210) to acquire one or more MR images from a desired target, a process (220) to determine MR-based fat characterization parameters, and process (230) to produce a fat characterization profile of the desired target. Process (210) can include performing MR imaging on an MRI machine, e.g., MRI machine (110), using 2D and 3D spoiled gradient echo sequences or other types of sequence. Process (220) can include implementing an exemplary model of the signal versus echo time that includes estimation of parameters, e.g., including the amount of water (water amplitude), the amount of fat (fat amplitude), initial phase ($\phi$), field inhomogeneity ($\Delta B_0$), T2 star (T2*), and the fat spectrum (e.g., by just employing NDB, discussed later). For example, implementation of process (220) can be performed on exemplary system MR-based fat characterization processing unit (120). Process (230) can include producing a fat characterization profile of the desired target by generating a relationship between fat, water, and other substances, e.g., by producing a map of the regions of fat, water, or fat and water in the MR image. Exemplary method (200) can implement exemplary processes (210), (220), and (230) in the order shown in FIG. 2A, or in any other order not shown in the exemplary figure.

FIG. 2B shows a block diagram of exemplary process (220) to determine MR-based fat characterization parameters. For example, process (220) can include a process (221) that selects the initial values of the exemplary parameters that are entered into the model. The exemplary parameters can include water amplitude, fat amplitude, $\phi$, $\Delta B_0$, T2*, and NDB, for example. Process (220) can include process (222) that can determine an exemplary complex MR signal s(t) from an model shown in Equations (1)-(3). Process (220) can include process (223) that estimates the values of the exemplary parameters in the model that minimize error between the simulated signal and measured signal.

Estimation can be performed by curve-fitting the signal to a mathematical model using nonlinear least squares techniques (such as Gauss-Newton or Levenberg-Marquardt). For example, the complex MR signal s(t) is curve-fitted as a function of echo time (t) and six unknown parameters to the following mathematical model:

$$s(t) = [w \cdot \alpha(t) + f \cdot \beta(t)] \cdot \exp(i\phi) \cdot \exp(-R2^* t) \cdot \exp(i\Delta B_0 t) \quad \text{(Eq. 1)}$$

$$\alpha(t) = a_{water} \cdot \exp(i\omega d_{water} t) \quad \text{(Eq. 2)}$$

$$\beta(t) = \Sigma a_j(NDB) \cdot \exp(i\omega d_j t) \quad \text{(Eq. 3)}$$

where $a_{water}$ and $a_j$ represent the number of protons in water and fat (see Table 1), $d_j$ represents the chemical shifts (shown in Table 1), and $\omega = 2\pi \cdot 42.576 \times 10^6 \, B_0$ rad s$^{-1}$ is the Larmor frequency. Unknown parameters include field inhomogeneity ($\Delta B_0$), transverse decay (R2*), initial phase ($\phi$), number of double bonds (NDB), water (w) and fat (f). Of these exemplary unknown parameters, $\Delta B_0$, R2* and NDB can be determined iteratively and the others algebraically using a phase constrained least squares technique (described later in the patent document). Bound constraints can be employed, such as $-1$ kHz $\leq \Delta B_0 \leq +1$ kHz, $0 \leq R2^* \leq 1$ ms$^{-1}$, and $1 \leq NDB \leq 6$. Two deterministic formulas can be used to fix CL and NDDB in relation to NDB (described later in the patent document).

Upon determining the minimal error of the exemplary parameters, process (224) can match the exemplary simulated signal s(t) against an actual MR signal obtained from the acquired MR image (e.g., the MR image acquired in process (210)). Process (220) can be an iterative process in which the error between the simulated signal and the obtained signal is minimized. Estimation of the exemplary parameters in process (220) can be performed simultaneously for all the parameters. Referring back to FIG. 2A, process (230) can include generating exemplary fat characterization profile from the simulated MR signal s(t) from process (220) that spatially matches (e.g., spatial fat mapping) what the objects look like on the exemplary MR image.

Various implementations of the exemplary MRI methods of the disclosed technology can include techniques (e.g., implementations of algorithms) for separating water and fat that exploit differences in the precession frequency of protons in fat and water. The algorithms of the disclosed technology can be configured to be of a particular level of robustness and accuracy, e.g., for clinical use. The exemplary algorithms can include a priori knowledge of the fat spectrum from MR spectroscopy or other imaging methods that can help improve the accuracy of implemented MRI techniques of the disclosed technology.

While the chemical shifts of the 6+ peaks in fat are known, their amplitudes depend on the type of fat present. An exemplary algorithm of the disclosed MRI method can include estimations of each peak amplitude by adding 6+ unknown parameters to the algorithm, as well as incorporate estimations of other unknowns, e.g., $\Delta B_0$, T2*, water amplitude and initial phase. The complexity and data requirements for estimating 6+ peak areas can start to approach that of MR spectroscopy, where 1000 s of data points are typically needed.

The disclosed technology can include exemplary models of the fat spectrum that can be implemented to enable MRI imaging methods to measure particular parameters (e.g., NDB from fat peaks in MR spectra), which can be implemented, for example, in vivo with high resolution. Implementation of the disclosed technology using such techniques can map the properties of fat in a variety of living and nonliving things, e.g., humans (clinical patients and non patients), animals, food, experimental samples, etc.

Table 1 shows the fat spectrum that can be represented to include only three parameters, e.g., CL, NDB, and NDDB. Data represented in this exemplary table were determined at 37° C. It is noted that the location of H2O can vary with temperature.

TABLE 1

| Peak | Location (Chemical Shift) | Assignment | Type | Relative Magnitude of Peak Area (Number of Protons) |
|---|---|---|---|---|
| 1 | 5.29 ppm | —CH=CH— | Olefinic | NDB · 2 |
|   | 5.19 ppm | —CH—O—CO— | Glycerol | 1 |
| 2 | 4.2 ppm | —CH$_2$—O—CO— | Glycerol | 4 |
| 3 | 2.75 ppm | —CH=CH—CH$_2$—CH=CH— | Diacyl | NDDB · 2 |
| 4 | 2.20 ppm | —CO—CH$_2$—CH$_2$— | A-Carboxyl | 6 |
|   | 2.02 ppm | —CH$_2$—CH=CH—CH$_2$— | α-Olefinic | (NDB − NDDB) · 4 |
| 5 | 1.6 ppm | —CO—CH$_2$—CH$_2$— | B-Carboxyl | 6 |
|   | 1.3 ppm | —(CH$_2$)$_n$— | Methylene | [(CL − 4) · 6] − [NDB · 8] + [NDDB · 2] |
| 6 | 0.9 ppm | —(CH$_2$)$_n$—CH$_3$ | Methyl | 9 |
| — | 4.7 ppm* | H$_2$O | Water | 2 |

The described exemplary model can be used to measure a fat characterization profile in a subject (e.g., a clinical patient) in vivo with high resolution. This can enable mapping of the properties of fat in subjects, e.g., quantify the amount of fat. Also, a further dimension can be added to this analysis by giving the type of fat that is present, as well as the amount. For example, primary sites that could be imaged include tumors, liver, abdomen, shoulder and muscle. Also, for example, the value for NDB can be used to describe the composition of fat and assess patient status with regard to such diseases as cancer, heart disease, NASH, and type 2 diabetes.

Examples of the significance of the imaging method can include that fat depots can be interrogated with high resolution, as compared to needle biopsy or MR spectroscopy. In subjects with small amounts of fat or where the fat occurs in thin layers or at boundaries, imaging can provide definitive voxel localization and also provides the spatial distributional change in type of fat in the body.

In exemplary implementations, for example with human subjects, two further simplifications can be employed. For example, CL can be assigned a set value of 17.5 since CL is known to be consistent in human subjects (CL=17.5); and NDDB can, to a first approximation, be assumed negligible (e.g., polyunsaturated fats make up only around 20% in human tissues). Another exemplary approach is to relate CL and NDDB to NDB by deterministic formulas (described later in the patent document). At this level of exemplary approximation, the single parameter NDB can characterize the entire fat spectrum. Employing this exemplary technique of adding one parameter (NDB) to the algorithm is far less burdensome for the estimation problem and overall implementation of MR imaging to determine fat properties.

Figure 3A:
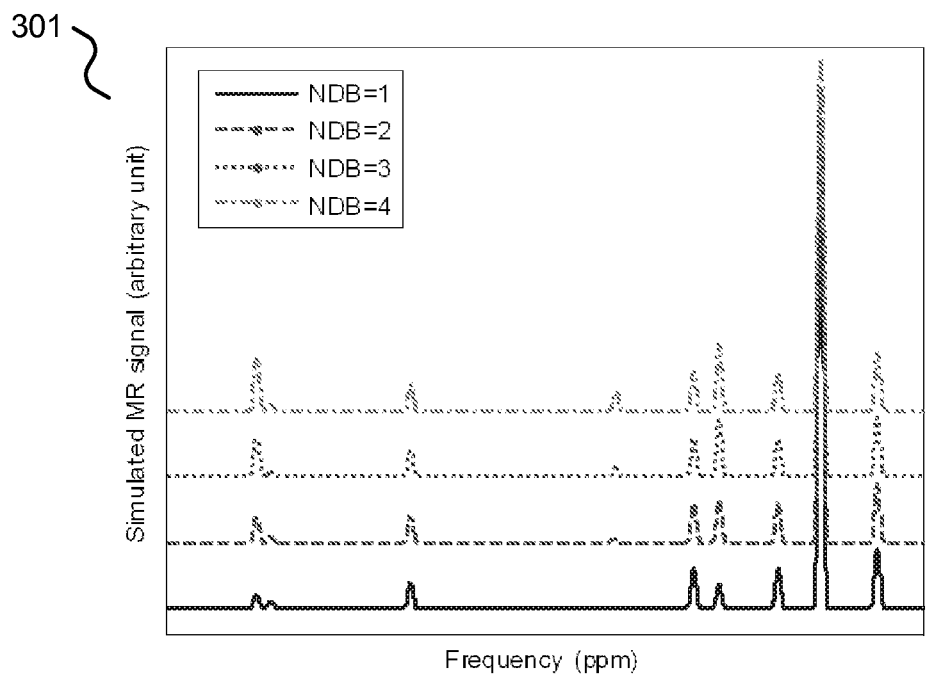
FIGS. 3A and 3B show exemplary graphs featuring different simulated fat spectra and free induction decay (fid) signals that are expected for different values of a number of double bonds (NDB).
Figure 3B:
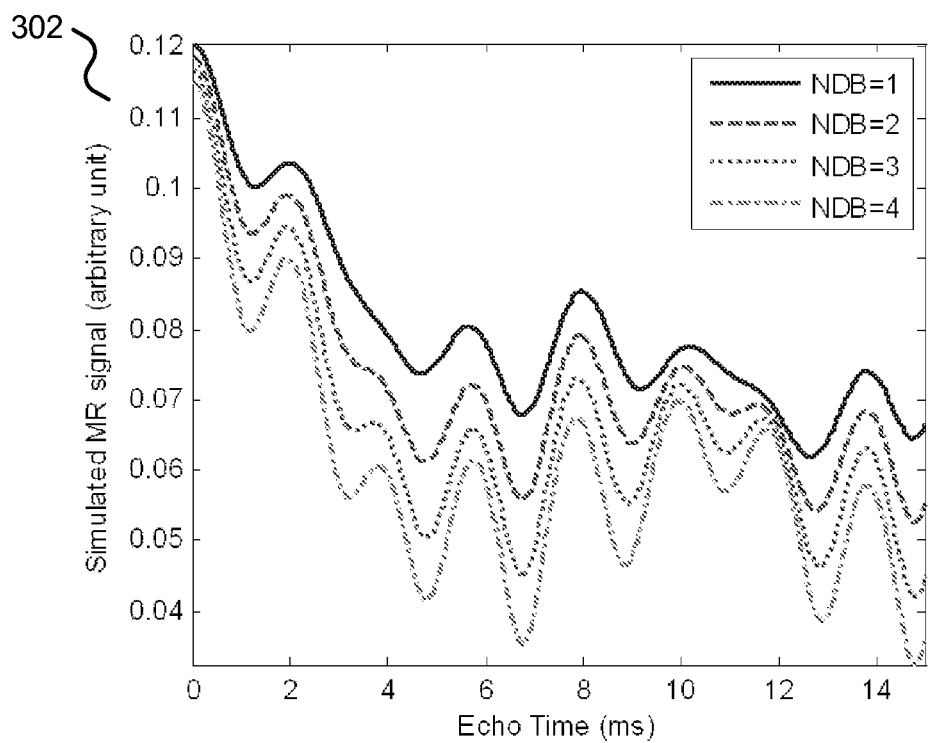

FIGS. 3A and 3B show exemplary plots featuring different simulated fat spectra and free induction decay (FID) signals that are expected for different values of NDB. FIG. 3A shows plot (301) of four simulated fat spectra expected for NDB=1, 2, 3, and 4. FIG. 3B shows plot (302) of four simulated FID signals expected for NDB=1, 2, 3, and 4. As seen in the exemplary plots, as NDB increases, the minor peaks tend to increase and the self-interference of fat becomes more pronounced (may appear like faster $T_2^*$ decay), which is the basis for being able to differentiate the types of fat.

In these exemplary experiments, two approximations can be made to reduce the number of unknowns by estimating CL and NDDB from NDB. Standard values of CL, NDB and NDDB in various fats and oils are shown in Table 2.

Table 2 shows the composition of various oils and fats as reported by the US Department of Agriculture (USDA). Composition data is shown by mass, and 100 g of substance contains the listed number of grams of fatty acids, and for human fats by MR signal (which is almost the same as the "by mass" composition). The mean CL, NDB and NDDB were calculated. "*" indicates an unusual data point.

TABLE 2

|  | Saturated | Mono-unsaturated | Di-unsaturated | Poly-unsaturated | CL | NDB | NDDB |
| --- | --- | --- | --- | --- | --- | --- | --- |
| Safflower Oil | 6.2 | 14.4 | 74.6 | 0.0 | 17.9 | 5.16 | 2.35 |
| Canola Oil | 7.4 | 63.1 | 19.0 | 9.1 | 18.0 | 3.91 | 1.14 |
| Sunflower Oil | 9.0 | 57.3 | 28.9 | 0.0 | 18.0 | 3.63 | 0.91 |
| Walnut Oil | 9.0 | 22.7 | 52.9 | 10.4 | 17.9 | 5.04 | 2.33 |
| Egg Yolk | 9.6 | 11.7 | 3.54 | 0.7 | 17.4 | 2.54 | 0.67 |
| Corn Oil | 12.9 | 27.6 | 53.5 | 1.2 | 17.8 | 4.35 | 1.76 |
| Sesame Oil | 13.7 | 39.7 | 41.3 | 0.3 | 17.8 | 3.89 | 1.32 |
| Olive Oil | 13.8 | 73.0 | 9.8 | 0.8 | 17.8 | 2.92 | 0.35 |
| Soybean Oil | 15.7 | 22.8 | 51.0 | 6.8 | 17.8 | 4.52 | 2.01 |
| Intralipid (20%) | — | — | — | — | 17.8 | 4.60 | 2.06 |
| Peanut Oil | 16.9 | 46.2 | 32.0 | 0.0 | 18.0 | 3.48 | 1.01 |
| Cod Liver Oil | 17.0 | 46.7 | 0.9 | 21.6 | 18.7 | 5.70 | 3.29 |
| Cottonseed Oil | 25.8 | 17.8 | 51.5 | 0.3 | 17.5 | 3.83 | 1.64 |
| Human Adipose | 27.1 | 49.6 | 23.4 | 0.0 | 17.5 | 2.89 | 0.70 |
| Chicken Fat | 28.6 | 44.1 | 19.5 | 1.1 | 17.4 | 2.78 | 0.70 |
| Human Marrow | 29.1 | 46.4 | 24.5 | 0.0 | 17.3 | 2.86 | 0.74 |
| Lard (Pork Fat) | 38.9 | 44.9 | 10.2 | 1.0 | 17.4 | 2.16 | 0.38 |
| Human Liver Fat | 46.8 | 42.6 | 10.6 | 0.0 | 17.4 | 1.92 | 0.32 |
| Tallow (Beef Fat) | 48.4 | 40.5 | 3.1 | 0.6 | 17.2 | 1.57 | 0.14 |
| Palm Oil | 48.9 | 37.0 | 9.1 | 0.2 | 17.0 | 1.76 | 0.30 |
| Butter* | 51.4 | 21.0 | 2.7 | 0.3 | 15.4 | 1.09 | 0.13 |
| Cocoa Butter | 58.7 | 32.8 | 2.8 | 0.1 | 17.4 | 1.23 | 0.10 |
| Palm Kernel Oil* | 81.5 | 11.4 | 1.6 | 0.0 | 13.5 | 0.46 | 0.05 |
| Coconut Oil* | 86.5 | 5.8 | 1.8 | 0.0 | 12.9 | 0.30 | 0.06 |

FIG. 4A shows an exemplary plot (401) that represent CL as a function of NDB in various oils and fats. In the case of CL, a linear trend is observed over most of the range. Plot (401) indicates a linear trend expressed by the exemplary formula CL=16.8+0.24 NDB. Unusual data points are represented as filled markers (and also shown in Table 2). For example, three oils at the low end of NDB (butter, coconut oil, palm kernel oil) have much shorter CL than would be predicted from the first relationship and are considered unusual data points (outliers).

FIG. 4B shows an exemplary plot (402) that represent NDDB as a function of NDB in various oils and fats. A non-linear relationship (e.g., a quadratic trend) is observed in the case of NDDB. Exemplary plot (402) indicates a quadratic trend expressed by the exemplary formula NDDB=0.092 $NDB^2$. Overlaid over the quadratic behavior is a theoretical "allowed range" (shaded in grey). The shaded area was defined from particular considerations, e.g., fatty acids are predominantly saturated, mono- or di-unsaturated, which means there are 10 unique permutations of triglyceride; biological oils are a mixture of the 10 triglycerides; the right side of the shaded area indicates more mono-unsaturated fatty acids are present (e.g., olive oil is unusually high in mono-unsaturated) and the left side indicates more di-unsaturated; and cod liver oil is high in poly-unsaturated and hence falls outside the range. Unusual data points are represented as filled markers (and also shown in Table 2).

Overall in FIGS. 4A and 4B, in the range NDB=1 to 6, the heuristic formulas can be considered to describe the properties of most fats and oils including human tissues. The exemplary formulas can be used to determine (or approximate) CL and NDDB from NDB, and therefore can eliminate these two variables from the exemplary model of the disclosed technology.

Exemplary materials and process to describe triglyceride properties using the disclosed technology are described in further detail. In one example, MR scanning was performed on a 3.0 T Signa HDx (GE Healthcare, Milwaukee, Wis.) with maximum gradient 40 mTm$^{-1}$; maximum slew rate, 150 Tm$^{-1}$s$^{-1}$. Multiple gradient echos were acquired using a 3D spoiled gradient recalled echo sequence with flyback gradients. A protocol with 15 echos (3 interleaves×5 echos) was employed with 0.6 ms spacing with an initial echo time 1.2 ms. Other parameters included repetition time (TR) 13 ms, flip angle 2°, matrix 192, slice 8 mm, and bandwidth ±62.5 kHz. Seven phantoms were created from oils and fats with different numbers of double bonds: canola, soybean, peanut, lard, safflower, olive, corn, peanut. A 20% Intralipid fat emulsion (Baxter Healthcare Corporation, Deerfield Ill.) was also used; the oil composition was obtained from the manufacturer (primarily soybean).

In these exemplary experiments, curve-fitting of the complex signal from the images was performed in MATLAB (Mathworks, Natick Mass.) using Gauss-Newton minimization of the least squares error. Fitted variables included $\Delta B_0$, $R2^*$, $\phi$, water amplitude, fat amplitude and NDB. Of these six variables, three were estimated by nonlinear search ($\Delta B_0$, $R2^*$, NDB) and the remainder were determined algebraically by a phase-constrained least squares method described later in the patent document. The two formulas above were used to fix CL and NDDB, e.g., CL=16.8+0.24 NDB and NDDB=0.092 NDB$^2$. Example fits are shown in FIGS. 5A and 5B.

Exemplary plot (501) shown in FIG. 5A includes curve fitted data for lard.

Exemplary plot (502) shown in FIG. 5B includes curve fitted data for safflower oil. As seen in both exemplary plots (501) and (502), there are substantial differences between the oils. For example, the dominant oscillation due to the olefinic protons is clearly stronger in safflower oil, as would be expected since the value of NDB is higher (5.16 versus 2.16, as shown in Table 2). Fitted values for all oil phantoms are given in Table 3.

Table 3 shows exemplary mean±standard deviation data of selected parameters (e.g, fat fraction (FF) and NDB) from inside regions of interest (e.g., 100 pixels) in MR images of the oil phantoms including Intralipid (20%), canola, peanut, soybean, safflower, lard, corn, and olive oils. NDB reference values from Table 1 are also shown.

TABLE 3

| | FF | NDB (imaging) | NDB (reference) |
|---|---|---|---|
| Intralipid (20%) | 0.213 ± 0.006 | 4.60 ± 0.34 | 4.60 |
| Canola | 1.005 ± 0.002 | 3.51 ± 0.10 | 3.91 |
| Peanut | 0.997 ± 0.001 | 2.99 ± 0.04 | 3.48 |
| Soybean | 1.001 ± 0.001 | 4.27 ± 0.04 | 4.52 |
| Safflower | 0.996 ± 0.002 | 4.94 ± 0.05 | 5.16 |
| Lard | 0.996 ± 0.002 | 2.49 ± 0.05 | 2.16 |
| Corn | 0.994 ± 0.001 | 4.38 ± 0.05 | 4.35 |
| Olive | 0.993 ± 0.002 | 2.44 ± 0.07 | 2.92 |

In these exemplary experiments, the fitted water and fat amplitudes were proportional to their proton densities. For example, MR fat quantification can give the relative proportion of protons from water and fat. While the ratio of fat and water by an MR signal can be very similar to ratio of fat and water by proton densities, the numerical similarity can depend on NDB and CL; and NDB and CL can vary for different fats and oils. A scaling that takes these differences into account is described below.

The number of protons in water is 2, and the molecular mass is 18. From Table 1, the number of protons in fat is 2+6 CL−2 NDB, and the molecular mass is 134+42 CL−2 NDB. To convert MR signal, which is proportional to number of protons, to a unit that is proportional to molecular mass, the following scalings are applied:

$$a_{water} = a_{water}/18 \quad \text{(Eq. 4)}$$

$$a_j = a_j/(134+42CL-2NDB) \quad \text{(Eq. 5)}$$

where 18 is the molecular mass of water and (134+42 CL−2 NDB) is the molecular mass of triglyceride. Now w and f represent water and fat in units proportional to the mass of each component, e.g. w=18 is equivalent to $a_{water}$ protons. The parameters may be combined into the fat fraction (FF), defined as FF=f/(w+f).

Figure 6:
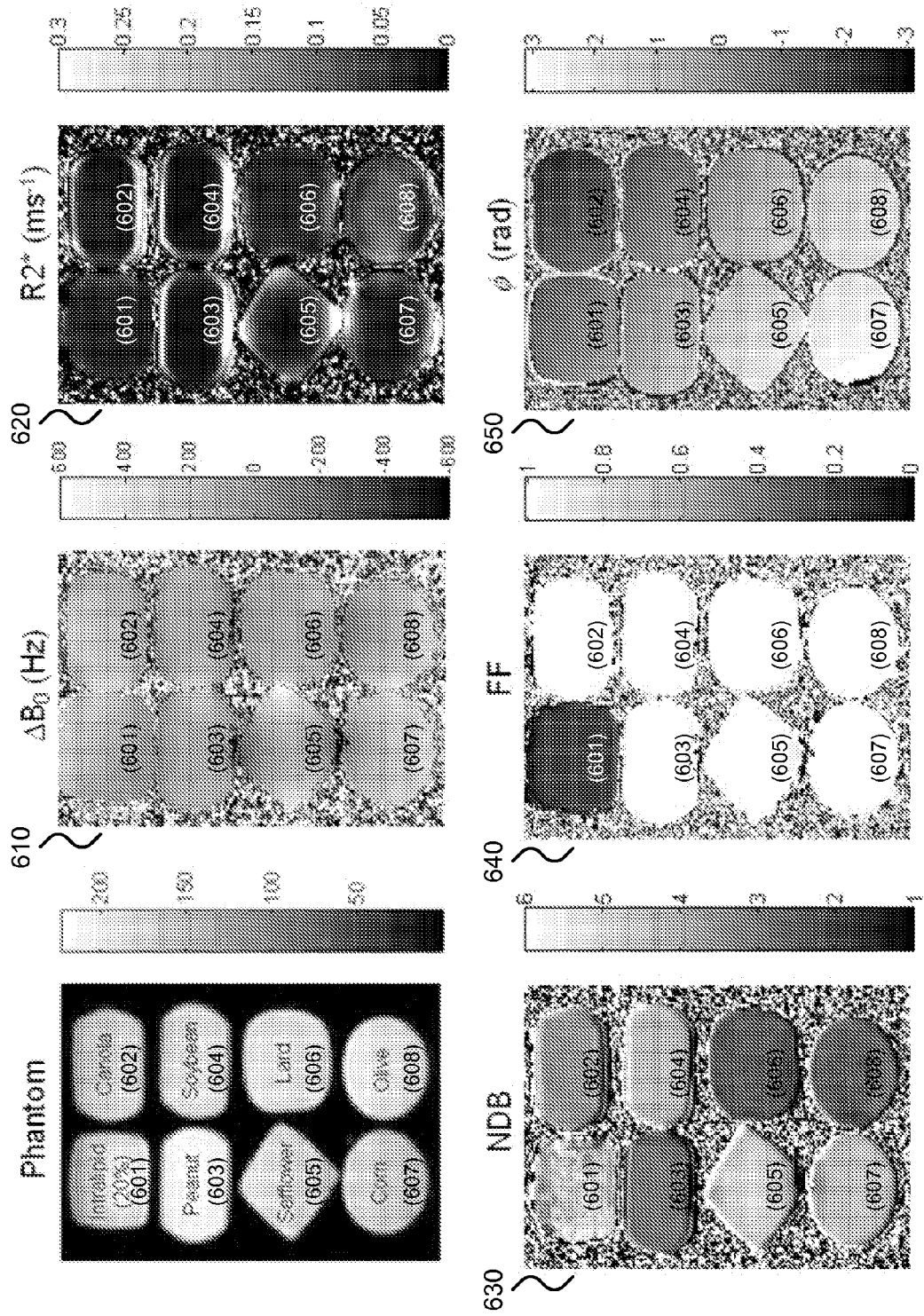
FIG. 6 shows exemplary phantoms and fitted maps showing exemplary parameters.

Exemplary results of the exemplary experiments implementing the disclosed technology to characterize triglyceride properties are described in further detail. In this example, several oils were obtained and constructed into a phantom, and imaging and analysis was performed to estimate the unknown variables in the model, as described above. FIG. 6 shows the exemplary phantoms and maps of the fitted variables, which can be generated by implementation of the exemplary method (200). Numerical values for the exemplary parameters are shown in Table 3, and the reference values are shown in Table 2. Correlation between the measurements can be considered strong (r=0.95) and significant (p<0.0002) with a slope of 0.95±0.12 and an intercept of 0.008±0.467.

As seen in FIG. 6, exemplary phantoms include Intralipid (20%) (601), canola (602), peanut (603), soybean (604), safflower (605), lard (606), corn (607), and olive (608) oils. Exemplary fitted maps of the variables $\Delta B_0$ (610), $R2^*$ (620), NDB (630), FF (640), and $\phi$ (650) are shown in FIG. 6. Numerical values for NDB from regions of interest inside the phantoms are given in Table 3. Note the properties of the fat are spatially mapped to their location.

Figure 7:
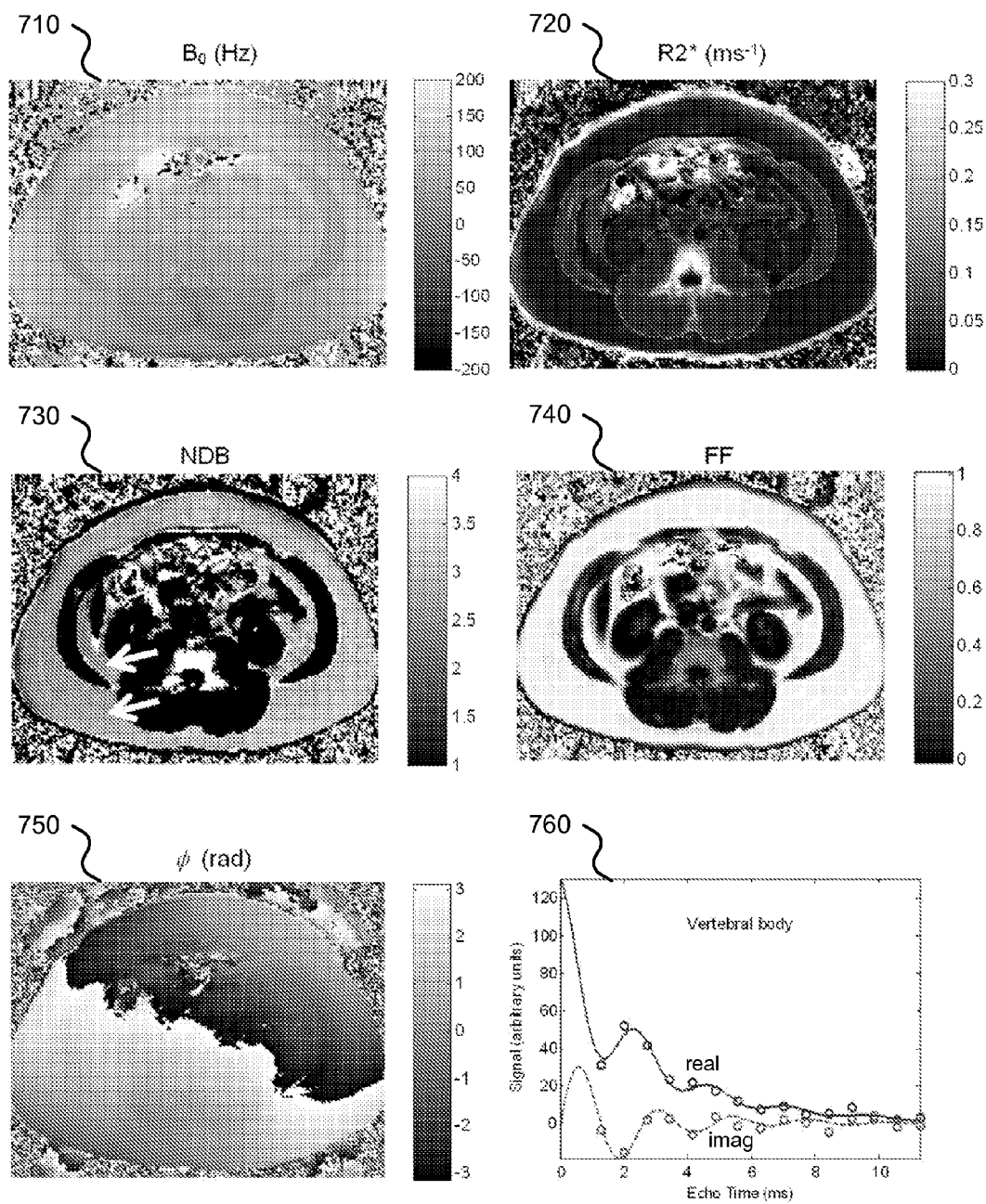
FIG. 7 shows an exemplary MRI sequence implementing the disclosed technology in a human subject.

FIG. 7 shows a demonstration of the feasibility of imaging with the same sequence in a human subject. Exemplary in vivo results of fitted maps are shown for the variables $\Delta B_0$ (710), $R2^*$ (720), NDB (730), FF (740), and $\phi$ (750). It is noted that the exemplary NDB map (730) is thresholded using a binary mask generated by (FF>0.2) to reject voxels containing small amounts of fat. Arrows in the exemplary NDB map (730) can indicate regions in deep subcutaneous and visceral fat. Plot (760) shows an exemplary signal versus echo time relationship, which demonstrates that in the vertebral body the signal decay is extremely rapid, which can limit the ability to estimate NDB (unrealistic values of NDB>6).

The exemplary experiments and implements of the disclosed technology to characterize the properties of triglyceride using chemical shift imaging have been shown to map the saturation level of triglycerides. Unlike MR spectroscopic imaging, wherein high resolution spectra are obtained at low spatial resolution, the use of the exemplary chemical shift imaging sequences using the disclosed technology can be used to provide high spatial resolution and low spectral resolution, which can benefit from a priori values to extract the spectral content of the MR signal.

The use of chemical shift imaging can be used in MR to help differentiate between water and fat. In some implementations, many of the subtle interactions can be neglected to make the calculations feasible, e.g., the fat spectrum can be simplified as a single peak at 1.3 ppm. The minor peaks make up approximately 30% of the total fat signal, and their relative areas can be indicative of the CL, NDB and NDDB in the fat molecule. The disclosed technology can add an additional variable to characterize the minor peaks in fat based on an exemplary model of the spectrum and two heuristic relationships. Results indicated using this exemplary approach can accurately and robustly measure NDB in fats and oils. Exemplary human imaging has been shown to be feasible.

In another aspect of the disclosed technology, an exemplary triglyceride model can be implemented for in vivo human liver fat proton ($^1$H) magnetic resonance spectrum characterization. The exemplary triglyceride model uses particular parameters that include number of double bonds (—CH═CH—) (NDB), number of methylene-interrupted double bonds (—CH═CH—CH$_2$—CH═CH—) (NMIDB), and average fatty acid chain length (CL). This aspect of the disclosed technology featuring the exemplary triglyceride model can be used characterize human liver fat spectra, which can allow for more accurate determinations of liver fat fraction from MR imaging and spectroscopy.

The liver plays a critical role in regulating metabolic homeostasis. For example, derangements in liver function can lead to abnormal intrahepatic triglyceride storage, leading to fatty liver disease. Proton Magnetic Resonance Spectroscopy ($^1$H MRS) is one method used to measure intrahepatic fat in vivo non-invasively and has been increasingly used as an endpoint in clinical trials and observational studies. Each of the multiple resonance peaks present in the exemplary fat $^1$H MR spectrum (shown in FIG. 8) represents structurally distinct proton moiety (as shown in Table 4). However, due to insufficient spectral resolution at clinical field-strengths, resolution of the individual components of the main clinically-observed fat peaks may not be possible (e.g., fat peaks 4 and 5 shown in FIG. 8 and Table 4). The observed ppm of these peaks represents the weighted position of the individual resonances. Also, the 4.2 and 5.3 ppm fat peaks can partially overlap, which may not be clearly indistinguishable from the 4.7 ppm liver water peak. Misclassification of the 4.2 and 5.3 ppm fat peaks as water signal can lead to fat quantification error.

Characterization of the complete liver fat spectrum is important for accurate fat quantification using $^1$H MRS and for accurate quantification using MRI-based measurement techniques that incorporate the multi-peak spectral structure of hepatic triglycerides. Unlike single-voxel MR spectroscopy (such as $^1$H MRS), MRI-based techniques can allow regional heterogeneity to be examined in a single scan. However, existing MRI-based techniques cannot directly measure the fat spectrum, and therefore benefit from the incorporation of the actual $^1$H MRS spectrum. The disclosed technology includes MRI-based techniques to provide a correct spectral model of fat, e.g., an accurate liver fat fraction value, like that of $^1$H MRS. The types of triglyceride in the liver can be measured directly biochemically or with high field (500 MHz) NMR, for example. However, these techniques require invasive tissue samples collection, which is impractical for large numbers of human subjects. The disclosed technology includes MRI-based non-invasive techniques to provide a correct spectral model of fat. The disclosed technology includes a more practical approach to perform in vivo spectroscopy at clinical field strength (3 T) and use knowledge of the triglyceride chemical structure to determine the fat spectrum.

Figure 8:
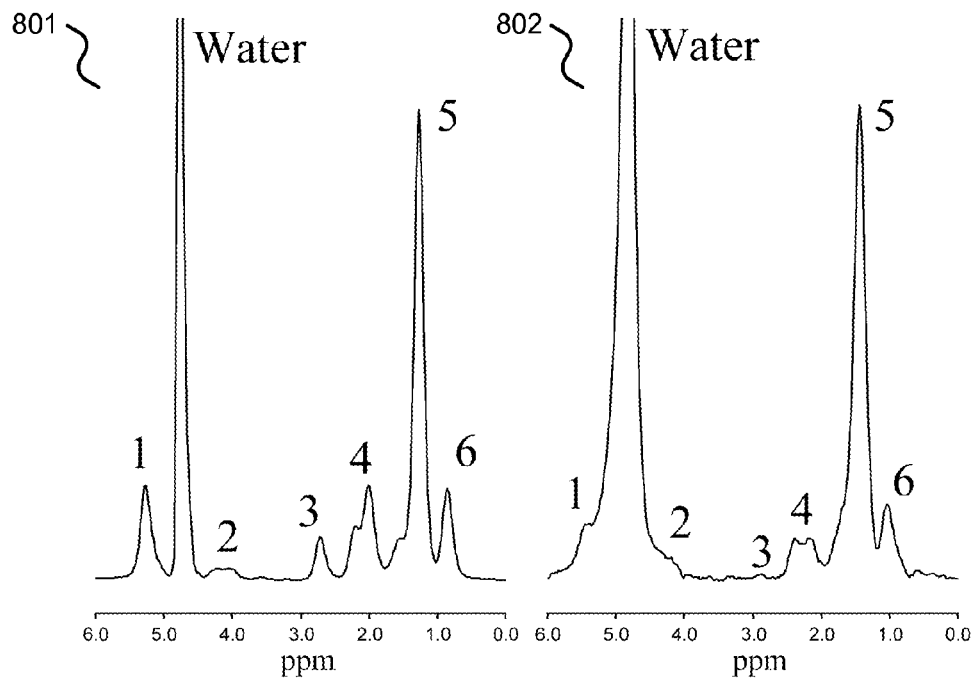
FIG. 8 shows multiple resonance peaks present in an exemplary liver fat $^1$H MR spectrum.

FIG. 8 shows Microlipid fat-water emulsion phantom MR spectrum (801) and in vivo liver MR spectrum from a human subject with fatty liver (802) at 3 T (TR 3500 ms, TE 10 ms). Fat Peak assignments are as follows: 1: —CH═CH— and —CH—O—CO—; 2: —CH$_2$—O—CO—; 3: —CH═CH—CH$_2$—CH═CH—; 4: —CO—CH$_2$—CH$_2$— and —CH$_2$—CH═CH—CH$_2$—; 5: —CO—CH$_2$—CH$_2$— and —(CH$_2$)$_n$—; and 6: —(CH$_2$)$_n$—CH$_3$. Of the exemplary six fat peaks resolvable by spectroscopy at 3 T, in vivo two peaks (peaks 1 and 2) are buried within the water peak and one peak (peak 3) is small and may be rarely seen in the human liver clinically.

Figure 9:
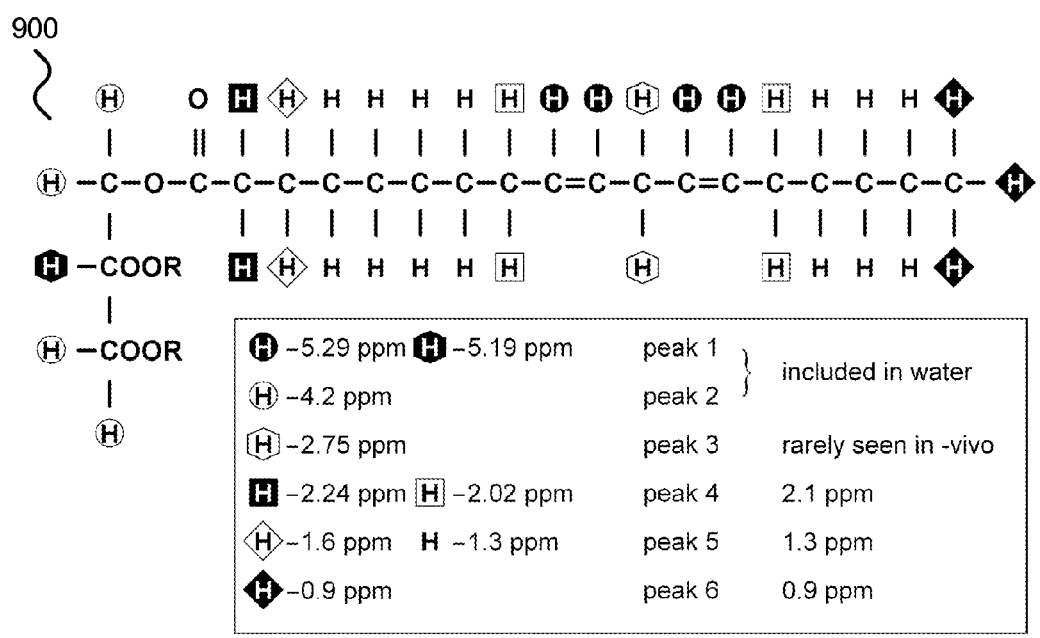
FIG. 9 shows the chemical structure of an exemplary triglyceride.

The chemical structure of an exemplary triglyceride (900) is shown in FIG. 9. The chain shown is linoleic acid. R indicates the other fatty acid chains in the triglyceride. In some instances, several resonances (at 5.29 and 5.19 ppm; 2.20 and 2.02 ppm; 1.6 and 1.3 ppm) are not resolvable in vivo at clinical field strengths (≤3 T) and appear as single peaks.

The relative magnitude of each of the resonances can be specified by three variables: number of —CH═CH— double bonds per molecule (NDB), number of double bonds separated by a single methylene CH$_2$ (NMIDB–number of methylene-interrupted double bonds), and the fatty acid chain length (CL). The peak assignments of triglyceride MR resonances with chemical shifts (at 37° C.) are shown in Table 4. Fat peak areas measurable at clinical field strengths (at 0.9 to 2.75 ppm) can alone suffice to determine NDB, NMIDB, and CL, from which relative magnitudes of the non-measurable 4.2 to 5.3 ppm fat peaks can be derived, and the complete liver $^1$H MR spectrum can be defined.

Table 4 shows peak assignments of triglyceride MR resonances with chemical shifts at body temperature (37° C.).

TABLE 4

| Peak | Location (Chemical shift) | Assignment | Type | Relative Magnitude of Peak Area (Number of Protons) | Observed ppm |
| --- | --- | --- | --- | --- | --- |
| 1 | 5.29 ppm | —CH═CH— | Olefinic | NDB * 2 | 5.3 ppm |
|   | 5.19 ppm | —CH—O—CO— | Glycerol | 1 |   |
| Water | 4.70 ppm | H$_2$O | — | — | 4.7 ppm |
| 2 | 4.20 ppm | —CH$_2$—O—CO— | Glycerol | 4 | 4.2 ppm |
| 3 | 2.75 ppm | —CH═CH—CH$_2$—CH═CH— | Diacyl | NMIDB * 2 | 2.75 ppm |
| 4 | 2.24 ppm | —CO—CH$_2$—CH$_2$— | A-Carboxyl | 6 | 2.1 ppm |
|   | 2.02 ppm | —CH$_2$—CH═CH—CH$_2$— | α-Olefinic | (NDB − NMIDB) * 4 |   |
| 5 | 1.60 ppm | —CO—CH$_2$—CH$_2$— | B-Carboxyl | 6 | 1.3 ppm |
|   | 1.30 ppm | —(CH$_2$)$_n$— | Methylene | [(CL − 4) * 6] − (NDB * 8) + (NMIDB * 2) |   |
| 6 | 0.90 ppm | —(CH$_2$)$_n$—CH$_3$ | Methyl | 9 | 0.9 ppm |

Implementation of the disclosed technology featuring the exemplary model can characterize the complete fat MR spectrum of human liver by determining the magnitude of non-measurable fat peaks directly from measurable fat peaks and knowledge of the chemical structure of triglycerides. This exemplary approach is validated in a fat-water emulsion phantom (e.g., materials or objects that are composed of materials that exhibit an MR signal that is used as a non-human standard), as well as is used to determine the fat spectrum in human subjects.

Exemplary experiments and validation procedures were performed, which included acquiring five 3 Tesla (3 T) single-voxel stimulated echo acquisition mode (STEAM) spectra with consecutively at progressively longer TEs in a fat-water emulsion phantom and human subjects (n=121) with known or suspected non-alcoholic fatty liver disease (NAFLD). T2-corrected peak areas were calculated, and phantom data were used to validate the exemplary model. Human data were used in the exemplary model to determine the complete liver fat spectrum.

Exemplary materials and process to implement the disclosed technology featuring the exemplary triglyceride model are described in further detail. For example, $^1$H MRS spectra acquisition from phantoms and in vivo (human subjects) using a 3 T MR signal (GE Signa EXCITE HD, GE Healthcare, Waukesha, Wis.). A 20×20×20 mm voxel was selected and shimmed after conventional imaging. The STEAM sequence (with an acquisition bandwidth of 5 kHz) was chosen to allow a shorter minimum echo time (TE), minimizing J-coupling effects. Five spectra were acquired consecutively at progressively longer TEs of 10, 15, 20, 25 and 30 ms in a single acquisition. The mixing time (TM) for the STEAM sequence was fixed at a minimum value of 5 ms. The TM and range of TE values was also chosen to minimize J-coupling effects. A repetition time (TR) of 3500 ms was chosen to minimize T1 effects. Multi-TE acquisition can allow for calculation of T2 and T2-corrected area of individual spectral peaks, as the different fat peaks can have different T2 values. In the exemplary experiments, there was no water saturation, and spatial saturation bands around the voxel were disabled to ensure a uniform spectral response across the frequency range of interest.

Exemplary analysis of the acquired MR spectra used nonlinear least squares curve-fitting as implemented in the AMARES algorithm (Advanced Method for Accurate, Robust and Efficient Spectral fitting) included in the MRUI (Magnetic Resonance User Interface) software package. All the observed or measurable fat peaks were modeled by multiple Gaussian resonances. The 1.3 ppm peak was modeled by three Gaussians; the fat peaks at 2.1, and 0.9 ppm were each modeled by two Gaussians, while the 2.7 ppm peak was modeled by a single Gaussian. The water and fat peaks in the 4-6 ppm range were modeled by five unconstrained Gaussians (e.g., the amplitude, linewidth or frequency of the peaks were all fitted freely). The T2-values of the spectral peaks and the T2-corrected peak areas were calculated by non-linear least-square fitting that minimized the difference between the observed peak areas and values given by theoretical decay.

For phantom data in the exemplary experimentation and validation, exemplary materials and process to implement the disclosed technology featuring the exemplary triglyceride model are described. The experimentally measured spectrum of a fat-water emulsion phantom (Microlipid®, Nestle HealthCare Nutrition, Inc., Minnetonka, Minn.) was compared to the results determined by implementation of the exemplary triglyceride model using the chemical structures (e.g., CL, NMIDB, NDB). Microlipid® was chosen as an exemplary phantom because the distribution of fatty acid chains in its constituent triglycerides was provided by the manufacturer.

The relative area of each of the peaks was found by adding the number of hydrogen nuclei with that type of bond in the triglyceride molecule. For example, each of the 3 fatty acid chains was terminated by a $CH_3$ giving a total signal of 9 signal units for the 0.9 ppm peak (as shown in the Relative Magnitude column of Table 4). Similarly, as each double bond had two CH groups associated with it, the 5.3 ppm peak was given by 2*NDB. However as virtually all fats are mixtures of different triglycerides, for each of the constituent triglycerides the number of hydrogen nuclei was weighted by the molecular fraction of the triglyceride type to give a mean CL, NDB and NMIDB.

As per the manufacturer, the distribution of fatty acid types in Microlipid fat-water emulsion is equivalent to a mean fat molecule with CL=17.86, NDB=5.04, and NMIDB=2.35. Using these CL, NDB, and NMIDB values in the spectral model described in Table 4, theoretical peak areas of that phantom were calculated (as shown in Table 5).

Table 5 shows exemplary T2s, and measured and reported peak areas for Microlipid fat-water emulsion phantom.

TABLE 5

| Peak | Observed ppm | Reported Area | T2 (ms) | Measured Peak Area |
|---|---|---|---|---|
| 1 | 5.3 ppm | 0.207 | 38.7 | 0.212 |
| 2 | 4.2 ppm | 0.075 | 25.4† | 0.097† |
| 3 | 2.75 ppm | 0.088 | 41.5 | 0.086 |
| 4 | 2.1 ppm | 0.314 | 41.9 | 0.307 |
| 5 | 1.3 ppm | 1.000 | 46.0 | 1.000 |
| 6 | 0.9 ppm | 0.168 | 71.4 | 0.161 |

†Values considered unreliable due to J-coupling.

STEAM MR spectroscopy was performed on the Microlipid phantom using a head coil with eight signal averages and one pre-acquisition excitation. When fitting the phantom spectra, all the Gaussians peaks were left unconstrained. The T2-corrected area of the individual fat peaks was expressed as a fraction of T2-corrected area of the main $CH_2$ (1.3 ppm) peak. The measured peak areas from spectroscopy were compared to the reported peak areas calculated according to the chemical structure, given by Table 4.

For the human subject data in the exemplary experimentation and validation, exemplary materials and process to implement the disclosed technology featuring the exemplary triglyceride model are described. One hundred thirty-six human subjects were recruited from clinical NAFLD studies being conducted at our institution. These subjects either had biopsy proven NAFLD, or were at risk for NAFLD due to family history or obesity. Fifteen subjects with known liver disease other than NAFLD were excluded from the study. The remaining 121 subjects (42 adult males, 57 adult females, 17 pediatric males, and 5 pediatric females) with mean ages of 44.3 years (adult subjects) and 14.2 years (pediatric subjects) were enrolled and underwent research MR examinations of the liver. As most of these subjects had no liver biopsy taken, differentiation between those with simple steatosis versus steatohepatitis was not attempted.

In this example using multiplanar localization images, a 20×20×20 mm voxel was selected within the right lobe of the liver parenchyma that avoided liver edges as well as large biliary or vascular structures. Following shimming during free breathing, STEAM spectroscopy was performed with an 8-channel torso array coil. Following a single pre-acquisition excitation, five spectra were acquired with a single average at each TE in a single 21 sec breath-hold. The spectra from the individual channels were combined using a singular value decomposition based approach. For every subject, this exemplary procedure was repeated two more times with identical parameters. Thus a total of three co-localized multi-TE spectra were acquired for each subject.

As the liver spectra had lower signal-to-noise than the Microlipid phantom, in the MRUI fitting of the spectra, the frequency of the fat peaks was fixed relative to the main $CH_2$ peak at 1.3 ppm. In this example, T2 decay was assumed to be monoexponential. Also, it was assumed the TE range used was short enough such that any errors introduced by J-coupling were negligible, and can be ignored. For each of the three multi-TE spectra, the water peak and measurable fat peaks 4, 5, and 6 were corrected for T2 decay. The T2-corrected area of peaks 4, 5, and 6 was averaged over the three spectra acquired for each subject.

In the exemplary experiments with human subject data, the in vivo examinations showed fat peaks 1 and 2 were not measurable due to the superimposed water peak. In subjects with low liver fat levels, T2 values of peaks 4 and 6 were difficult to estimate precisely. In these cases, peak areas were determined by correcting the TE 10 ms spectrum using a mean T2-value derived from the subjects whose T2 could be determined. Peak 3 was only detectable in subjects with the greatest levels of fat in the liver, due to the low levels of polyunsaturated fat in the liver. Thus, subjects with a T2-corrected peak area of $CH_2$ (1.3 ppm) greater than 40% of the T2-corrected water peak area were used to describe the behavior of this peak relative to the other fat peaks. It was then assumed that this behavior can be typical for all subjects.

Relative areas of measurable fat peaks (peaks 3-6) were used to generate mean NDB, NMIDB and CL values for a "mean" liver triglyceride molecule. This allowed the area of peaks 1 and 2 to be calculated, giving the fraction of the fat signal buried under the water peak. The T2-corrected area of peaks 4 and 6 were plotted with respect to T2-corrected peak areas of peak 5. Linear least-square fits of the data were calculated and quality of fit was evaluated by the Pearson-r correlation coefficient to examine the variability in the ratio of the peak areas seen in the liver.

Results of the exemplary experiments and validations of the disclosed technology featuring the exemplary triglyceride model using phantom and human subject data are described in further detail. Table 5 shows exemplary comparisons of the T2-corrected peak areas of the Microlipid fat-water emulsion phantom given by spectroscopy with those given by the exemplary triglyceride model. Using the T2-corrected areas of peaks 3-6 of the phantom in the exemplary triglyceride model, the parameters are determined as CL=18.44, NDB=5.19, and NMIDB=2.40 (which can be compared to reported values of CL=17.86, NDB=5.04, and NMIDB=2.35). The CL, NDB and NMIDB values generated from peaks 3-6 can give an expected peak 1 area of 0.204, which can be considered in close agreement with measurement and reported peak areas. In this exemplary experiment, the measured area of peak 2 does not match that of the model-predicted or that of the generated using peaks 3-6. This peak can be considered to be strongly J-coupled resulting in T2 underestimation and hence peak area overestimation.

Figure 10:
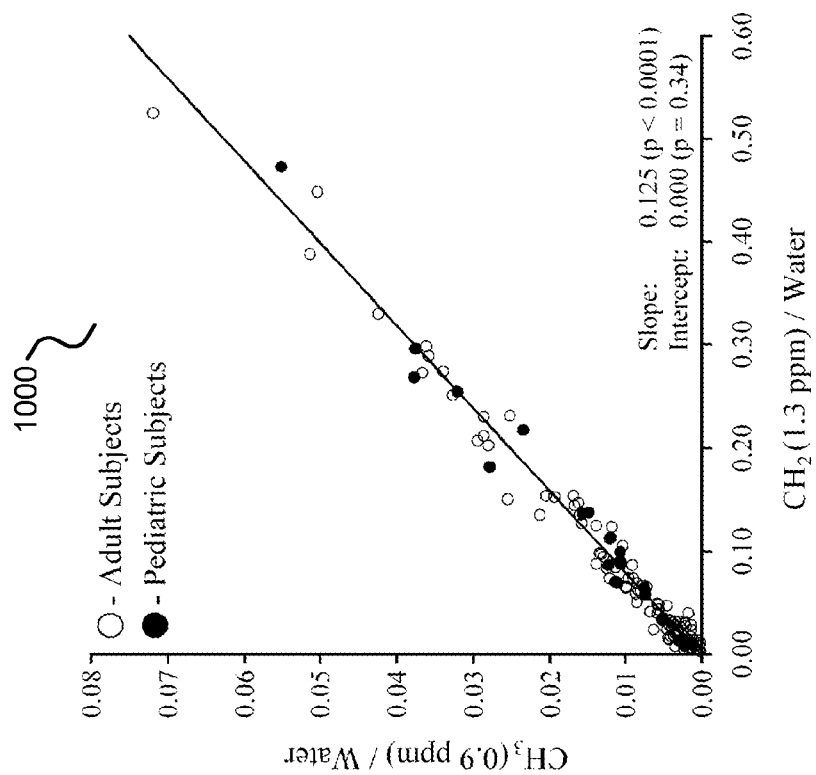
FIG. 10 shows an exemplary comparison of T2-corrected peak areas of peaks 5 and 6 in vivo.

FIG. 10 shows exemplary plot (1000) comparing the T2-corrected peak areas of peak 6 area ($CH_3$ at 0.9 ppm) with peak 5 area ($CH_2$ at 1.3 ppm) in pediatric and adult human subjects in vivo. Based on these exemplary results, there is a strong linear correlation (r=0.989) between the two values, with a ratio of those peak areas values of 0.125 (p<0.0001; intercept=0.000, p=0.34).

Figure 11:
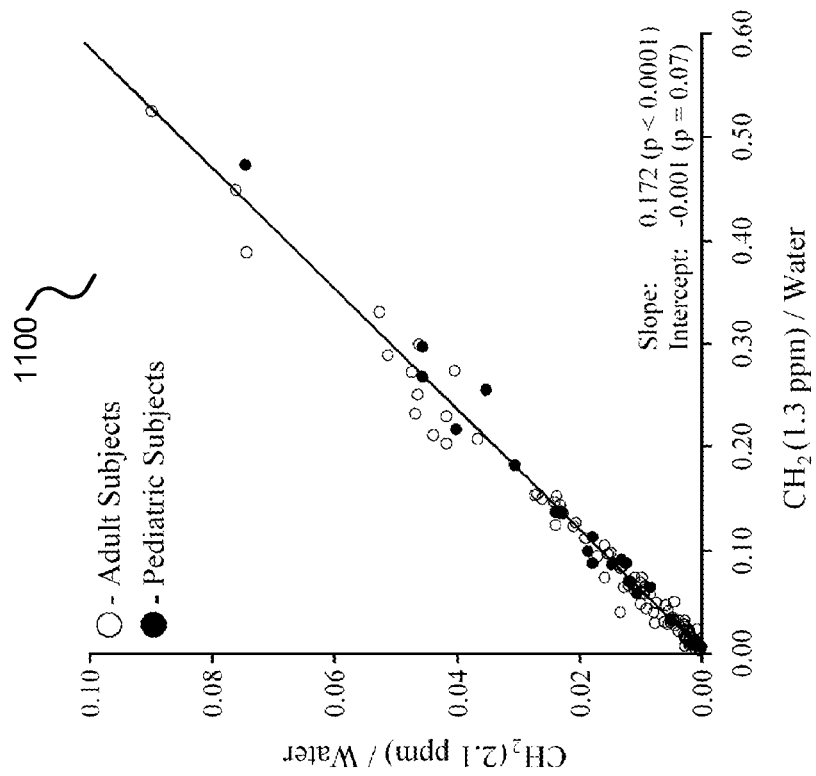
FIG. 11 shows an exemplary comparison of T2-corrected peak areas of peaks 4 and 5 in vivo.

FIG. 11 shows exemplary plot (1100) comparing the T2-corrected peak areas of peak 4 area ($CH_2$ at 2.1 ppm) with the peak 5 area ($CH_2$ at 1.3 ppm) in pediatric and adult human subjects in vivo. Based on these exemplary results, the ratio of the area of peak 4 to peak 5 is 0.172 (p<0.0001: intercept=−0.001, p=0.07), and there is strong linear correlation (r=0.991) between the two values. It is noted that there were only 4 subjects in the exemplary study with T2-corrected peak 4 area fat ratios >40% (fat fractions 0.368, 0.392, 0.409 and 0.443). In these subjects the mean T2-corrected area of peak 3 (2.75 ppm) peak was determined to be 0.9% (range 0.7-1.1%) that of the T2-corrected area of peak 5.

Using these relative peak areas into the exemplary model shown in the Relative Magnitude of Peak Area column of Table 4, the mean liver triglyceride molecule had the following parameters: CL=17.45, NDB=1.92 and NMIDB=0.32. In one example, assuming that fat consists entirely of saturated, monounsaturated and diunsaturated fatty acid chains, human liver fat is about 46.8% saturated, 42.6% monounsaturated and only 10.6% diunsaturated.

The mean human liver spectrum, including calculated areas of peaks underlying water or those unresolvable in vivo, is shown in Table 6. Implementation of the exemplary model (from Table 4) indicates that the fraction of fat under the water peak (peaks 1 and 2) is 8.6% of the sum of all the fat peaks. Using this correction, the mean fat fraction in the human subject group was 0.107 with values ranging from 0.004 to 0.443.

Table 6 shows the exemplary liver fat spectrum, using the areas of peaks 3, 4, 5 and 6 to extrapolate the areas of peaks 1 and 2 and the full fat spectrum.

TABLE 6

| Peak | Observed ppm | T2 (ms) | % total fat signal | Location | % total fat signal |
|---|---|---|---|---|---|
| 1 | 5.3 ppm | — | 4.7% | 5.29 ppm | 3.7% |
|   |         |   |      | 5.19 ppm | 1.0% |
| Water | 4.7 ppm | 23 | — | 4.70 ppm | — |
| 2 | 4.2 ppm | — | 3.9% | 4.20 ppm | 3.9% |
| 3 | 2.75 ppm | 51 | 0.6% | 2.75 ppm | 0.6% |
| 4 | 2.1 ppm | 52 | 12.0% | 2.24 ppm | 5.8% |
|   |         |    |       | 2.02 ppm | 6.2% |
| 5 | 1.3 ppm | 62 | 70.0% | 1.60 ppm | 5.8% |
|   |         |    |       | 1.30 ppm | 64.2% |
| 6 | 0.9 ppm | 83 | 8.8% | 0.90 ppm | 8.8% |

In the aforementioned exemplary phantom-human validation study, the disclosed technique featuring a molecular structure-based method for MR spectral characterization was validated in a mixed fat emulsion phantom of known composition. This exemplary method can be applied to human subjects to determine a mean liver fat MR spectrum, including the peaks not directly measurable in vivo.

The results of exemplary experimentation, e.g., the phantom study, show that the exemplary model can accurately derive the complete fat-water emulsion MR spectrum. In the exemplary results, peak 2 was strongly coupled AB spin system, meaning its behavior may heavily be affected by J-coupling even at short TEs, leading to T2 underestimation and peak area overestimation. However, from Table 4, peak 2 has a fixed relative magnitude of 4, and thus can be deduced from other peak areas and does not require accurate measurement. It is valid to deduce the entire fat spectrum from the peaks that are resolvable from water.

The exemplary results suggest that, regardless of the level of fat deposition, there may only be limited variation in the liver fat spectrum. As shown in FIGS. 10 and 11, when the areas of peak 4 or 6 are compared to peak 5, similar Pearson-r correlation coefficient values were found. While peak 6 has fixed relative magnitude, peak 4 is more sensitive to changes in CL and NDB. The similar levels of scatter suggest that the variability is mainly due to noise rather than biochemical causes. The strong correlation between fat peak areas can also suggest that it is acceptable to use the relative area of peak 3 in high fat subjects as the value for all subjects. The exemplary results suggest that the fat spectrum is similar for steatosis and steatohepatitis.

The exemplary implementation (experiments and validation studies) of the disclosed technology showed verified that measurable $^1$H MRS fat peaks can be used for in vivo triglyceride and fat characterization, e.g., of a mean liver triglyceride molecule and hence derive the complete liver fat MR spectrum. This exemplary molecular structure-based method for fat spectral characterization can allow more accurate quantification of liver fat using spectroscopy and using MR imaging methods that incorporate spectral correction.

In another aspect, an exemplary algorithm is described for use in nonlinear least squares curve-fitting applied to fat-water modeling that further can constrain the phase of both species to be equal at an echo-time of zero. For example, the exemplary phase-constrained technique can estimate the amount of water and the amount of fat by selecting an initial phase of water and an initial phase of fat to be equal at an echo-time of zero. This exemplary phase-constrained water-fat separation technique includes the principle that the initial phase should be a property of the excitation pulse and receiver coil only. Some advantages of implementing the exemplary phase-constrained water-fat separation in MR imaging include improved noise performance and/or reduced data requirements (fewer echos).

Numerical modeling of the MR signal variation with echo-time can be used for estimating properties of water and fat. Implementations of numerical modeling can overcome many of the limitations of algebraic techniques, such as in-phase and out-of-phase imaging, that rely upon specific echo-times, a simplified fat spectrum and negligible T2* decay. In MR spectroscopy, there are typically thousands of acquired data points (echo-times), and thus analyses can be amenable to curve-fitting many tens of free parameters. Additionally, often only a single voxel may be considered, and user interaction can be expected to help initialize parameters and adjust fitting ranges. In comparison, the disclosed technology includes an exemplary chemical shift based water-fat separation MRI method that can acquire very few echos and operate upon tens of thousands of voxels.

Exemplary models of the disclosed technology can include up to six or more unknowns per voxel, which can comprise linear terms (e.g., complex water and fat) and nonlinear terms (e.g., field inhomogeneity, number of double bonds and T2*). For estimating the values of variables that are used in the exemplary model, the unknowns can be estimated by iterative nonlinear least squares search over a multi-dimensional parameter space to minimize the sum of squares difference between the model and the measured data points.

One exemplary technique that can improve reliability includes the use of separable least squares to obtain the linear terms at virtually no computational cost. This can reduce the dimension of the parameter space to the nonlinear terms only. For example, according to separable least squares, the linear terms can be obtained at each iteration of the nonlinear search by solving a linear equation, Equation (6):

$$Ax=b \quad \text{(Eq. 6)}$$

where A is a complex m×2 matrix representing the echo-time variation of water and fat, m is number of echos, x is a complex 2-vector representing water and fat, and b is a complex m-vector of acquired data points at different echo-times (corrected for the effects of field inhomogeneity and/or T2*).

With this exemplary linear formulation, water and fat are modeled as independent complex variables having their own amplitude and phase. The least squares estimate is obtained by Moore-Penrose pseudoinverse in Equation 7:

$$x_{lin}=(A^HA)^{-1}A^Hb \quad \text{(Eq. 7)}$$

However, this formulation is too general for the water-fat separation problem is presented. In many imaging sequences, water and fat are known to have the same phase at certain echo-times, which gives rise to the familiar in-phase/out-of-phase behavior. For example, images obtained at 3.0 T using a spoiled gradient recalled (SPGR) echo sequence are considered in-phase at 0.0, 2.3, 4.6 . . . ms.

Because of the complexity due to spectral modeling and J-coupling, water and fat are only truly in-phase at an echo-time of zero. At this point the initial phase is the same for water and fat and is a property of the receiver coil and radio frequency (RF) pulse. While this is certainly true for low flip angle and symmetric RF pulses, the initial phase may exhibit a dependence on the off-resonance frequency with some non-standard pulses. Phase accrual during the RF pulse is predictable from the chemical shift and may also be included in the model when necessary.

Applying a constraint that the phases should be equal at a certain echo-time can provide a better model of the MR physics and has advantages due to the fact that fewer parameters need to be estimated (e.g., two amplitudes and one phase rather than two amplitudes and two phases). A phase constraint can have advantages, such as reduced data requirements and reduction of noise errors. However, the linear least squares estimate of Equation (7) cannot be used, and so the common phase term can be included as a nonlinear parameter. This increases the dimension of the nonlinear parameter space, which can in turn reduce the speed and reliability.

A direct method for estimating the initial phase is described in this aspect of the disclosed technology that does not require curve-fitting and can enable fast and reliable calculation of this parameter. Implementations of linear and phase-constrained methods can be performed on simulated and acquired data to measure the noise properties and to demonstrate the feasibility of water-fat separation using small numbers of echos.

Exemplary process to implement the disclosed technology using the exemplary model with phase constraint features are described in further detail. For example, water and fat signals can be estimated either by linear least squares (Equation (7)) or by phase-constrained least squares using the formula given in Equation (8):

$$x_{pc}=Re(A^HA)^{-1}Re(A^Hbe^{-i\phi})e^{-i\phi} \quad \text{(Eq. 8)}$$

where initial phase $\phi=\frac{1}{2}\angle(A^Hb)^T Re(A^HA)^{-1}(A^Hb)$. Two key differences between Equation (7) and Equation (8) are the elimination of $Im(A^H be^{-i\phi})$ and the presence of $Re(A^H A)^{-1}$ rather than $(A^H A)^{-1}$. The elimination of the imaginary noise and possibly smaller condition number can indicate that the phase-constrained estimator should exhibit lower noise error than the linear.

An example is presented to solve Ax=b under the constraint that all elements of x have the same phase. A solution of the desired form is $x_{real}e^{i\phi}$, with real vector $x_{real}$ and real scalar $\phi$.

$$Ax_{real}e^{i\phi}=b \tag{Eq. A1}$$

For any value of $\phi$ the optimal least squares estimate of $x_{real}$ may be obtained by equating d $(r^H r)/dx_{real}$ to zero, where residual $r=b-Ax_{real}e^{i\phi}$.

$$\hat{x}_{real}=Re(A^H A)^{-1}Re(A^H be^{-i\phi}) \tag{Eq. A2}$$

This allows the residual to be expressed as a function of $\phi$ only.

$$r=b-ARe(A^H A)^{-1}Re(A^H be^{-i\phi})e^{i\phi} \tag{Eq. A3}$$

All that remains to minimize $r^H r$ with respect to $\phi$. Equating $d(r^H r)/d\phi$ to zero yields $$-2Im(A^H be^{-i\phi})^T Re(A^H A)^{-1}Re(A^H be^{-i\phi})=0 \tag{Eq. A4}$$

which is the imaginary part of $(A^H b)^T Re(A^H A)^{-1}(A^H b)e^{-i\phi}$. For the imaginary part of this expression to be zero the overall phase must be zero, which requires $$\hat{\phi}=\tfrac{1}{2}\angle(A^H b)^T Re(A^H A)^{-1}(A^H b). \tag{Eq. A5}$$

To demonstrate the use of the phase-constraint in separating water and fat in MR imaging, exemplary MRI data were acquired on a 3.0 T Signa HDx (GE Healthcare, Milwaukee, Wis.) using an 8-channel torso array. Four echos were acquired using a 3D SPGR sequence with flyback gradients at TE 0.92, 1.65, 2.38 and 3.10 ms. Other parameters were TR 8.3 ms, flip angle 6°, matrix 256, slice 8 mm, bandwidth±166 kHz and Array Spatial Sensitivity Encoding Technique (ASSET) factor 2. Abdominal scanning was performed on a volunteer who was known to have no liver fat. The SNR measured in the right lobe of the liver on the amplitude in-phase image was 18.1. Real and imaginary images were taken offline for processing, as described below.

A water-fat separation method was implemented in MATLAB (The Mathworks, Natick Mass.) using the Gauss-Newton algorithm with separable least squares and knowledge of the fat spectrum. The field map was parameterized as a $3^{rd}$-order polynomial defining a surface: $f(x, y)=\beta_0+\beta_1 x+\beta_2 y+\beta_3 x^2+\beta_4 y^2+\beta_5 xy+\ldots$ with 10 unknown coefficients ($\beta_j$). T2* was neglected, but may be included by allowing $\beta_j$ to be complex. Parameters were initialized to zero and typical final values were ±1. Numerical derivatives used a stepsize of $\sqrt{\epsilon}$ times the current value, or $\sqrt{\epsilon}$ if the value was zero, where $\epsilon \sim 10^{-7}$ is machine precision. The number of iterations was fixed at 20 although convergence was usually complete after 5 iterations.

Figure 12:
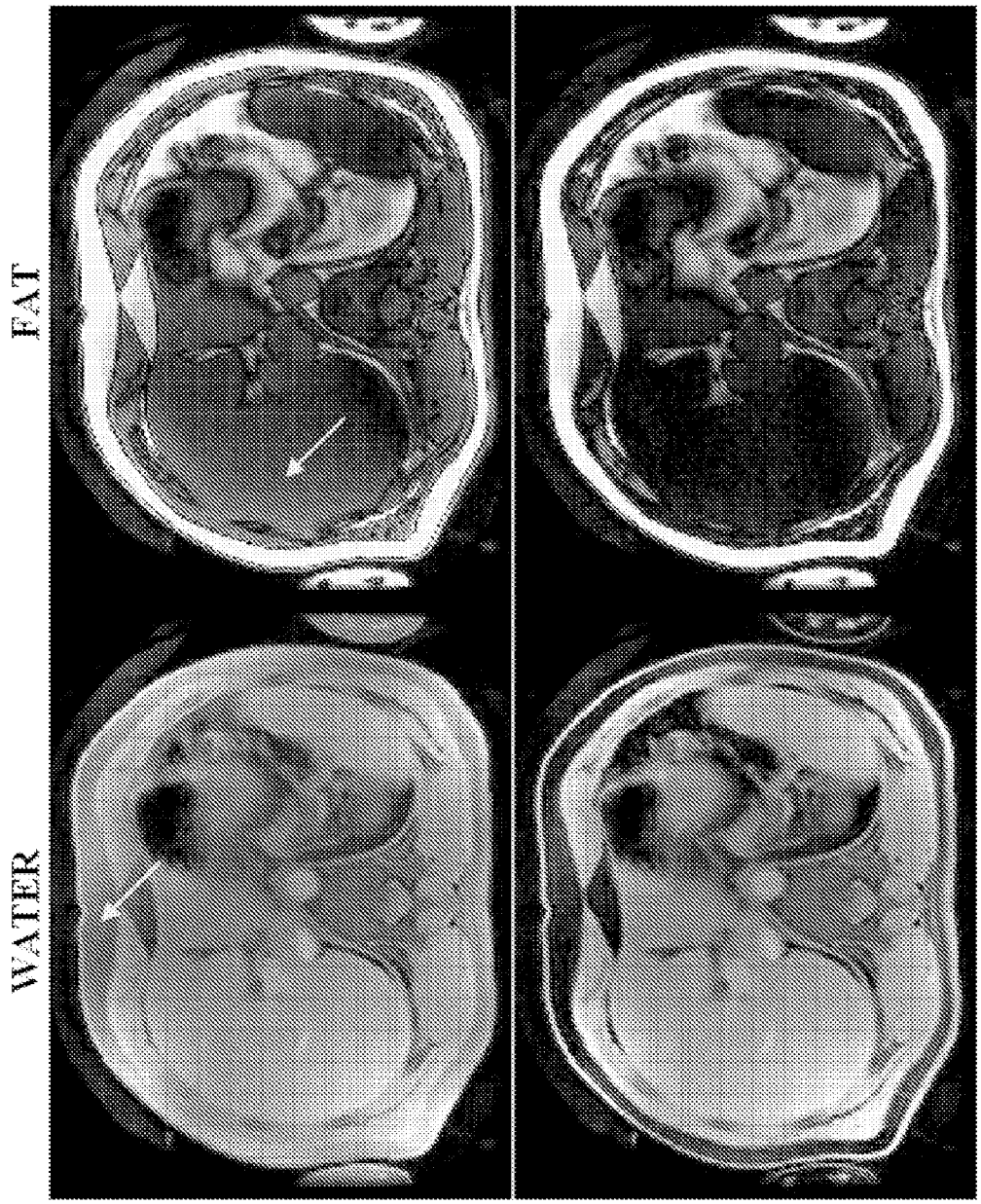
FIG. 12 shows MR images featuring separated water and fat images using two echos.

FIG. 12 shows image (1200) that includes MR images featuring separated water and fat images from reconstructions using two echos using the linear equation (Equation (7) (shown in the top row) and the phase-constrained equation (Equation (8) (shown in the bottom row). With only two echos, the exemplary linear method was shown to be unable to achieve separation, as there are more unknowns (five) than data points (four). Exemplary arrows indicate erroneous signals in the subcutaneous fat and in the liver (this subject is known to have no liver fat). The exemplary phase-constrained method reduces the number of unknowns by one and hence the values can be estimated reliably.

In FIG. 12, there are large differences between the linear and phase-constrained methods, particularly in the fat image. A simple count of the number of unknowns versus data points can confirm that the linear method should not be expected to simultaneously estimate water, fat and field map from two echos, e.g., there are five unknowns (amplitude and phase of water and fat plus the field map) versus four data points (real and imaginary parts of two echos). Thus there are insufficient degrees of freedom to estimate all the parameters. As a consequence these images are essentially uncorrected for the field map. The phase-constraint removes one of the unknowns, so a meaningful solution can be obtained.

Figure 13:
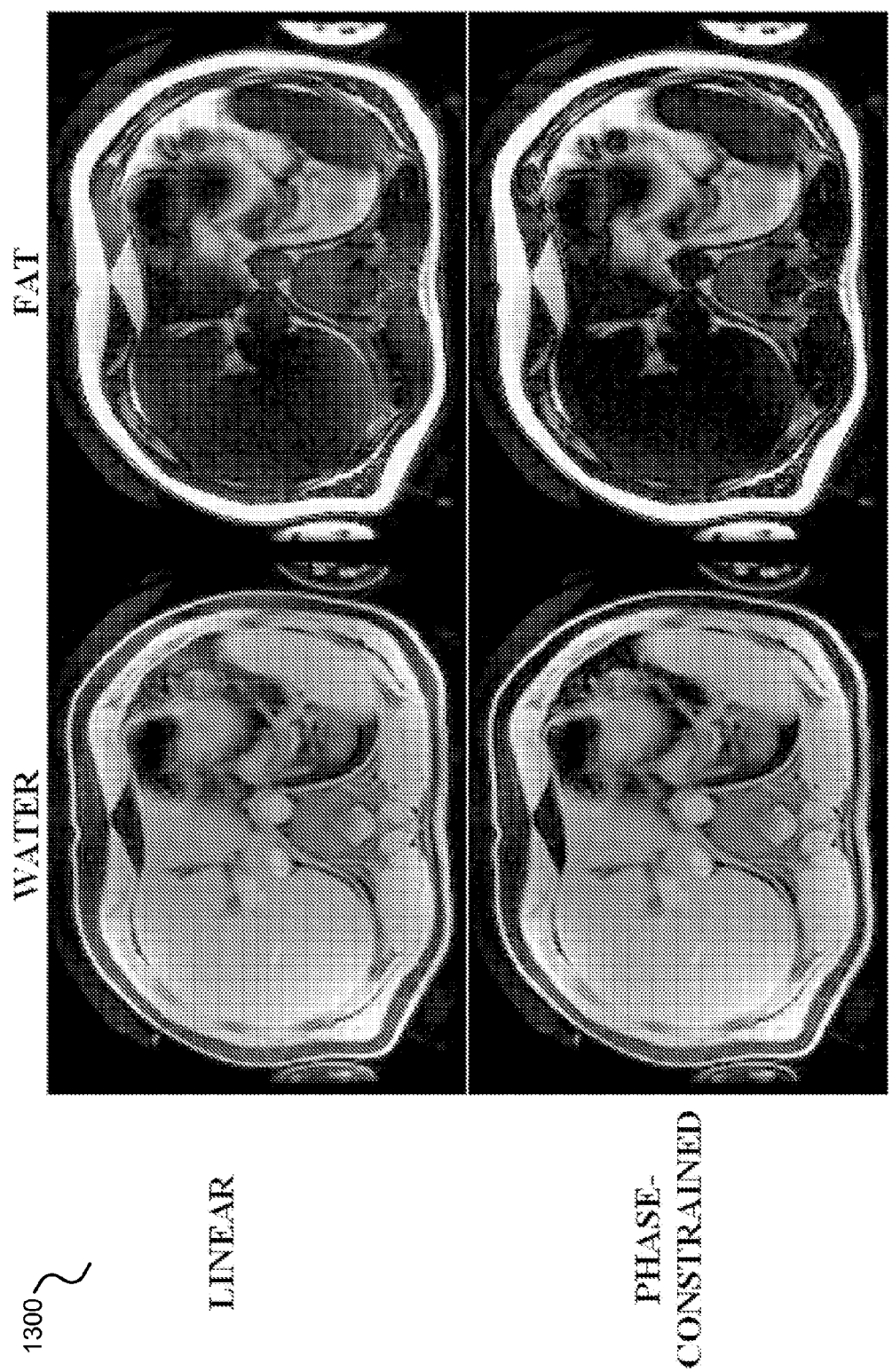
FIG. 13 shows MR images featuring separated water and fat images using three echos.

FIG. 13 shows image (1300) that includes MR images featuring separated water and fat images using three echos using the linear equation (Equation (7) (shown in the top row) and the phase-constrained equation (Equation (8) (shown in the bottom row). In this exemplary data set, the number of data points is six (real and imaginary parts of three echos), hence the linear and phase-constrained methods are both able to obtain meaningful solutions. Accordingly, differences in the images are less conspicuous although the SNR should be higher in the phase-constrained images. To verify this, regions of interest containing 100 pixels were drawn in the right lobe of the liver on the (complex) water and fat images. Ratios of the standard deviations (linear/phase constrained) in these regions were 1.02 for water and 1.50 for fat, which are close to the simulation values 1.00 and 1.41 at low fat fraction.

It is also noted that there is qualitative similarity in separation performance between the two echo phase-constrained and the three echo linear images (e.g., refer to FIG. 12 bottom row and FIG. 13 top row), which suggests the constraint can substitute for one echo. The quantitative noise performance, as measured by ratios of the standard deviations (two echo phase-constrained/three echo linear) is mixed: 0.81 for water and 1.16 for fat. While decreasing the number of echos from 3 to 2 should decrease the SNR by a factor of $\sqrt{2/3}\approx 0.82$, the loss is mitigated by up to $\sqrt{2}$ by the phase-constraint, hence the factor $\sqrt{2/3}\cdot\sqrt{2}\approx 1.15$. This can explain the results observed for water and fat at low fat fraction.

These results validate the exemplary implementation of the phase-constrained method for use in separating water and fat in chemical shift based imaging. Employing the exemplary phase-constraint method can include advantages such as fewer echos being required and random noise being reduced in the estimated parameters. Results from this exemplary implementation can confirm a reduction in noise standard deviation of up to $\sqrt{2}$.

The use of iterative curve-fitting can be slow and unreliable without good initial estimates. This may be partly because the sum of squares error is periodic in $\phi$ rather than quadratic, which can confound optimization algorithms. The disclosed exemplary phase-constraint method can eliminate this problem by computing the initial phase from an analytic formula (Equation (8)). While this may not necessarily help with curve-fitting other nonlinear terms in the model, e.g., the field map, it can enable the phase-constraint to be used without increasing the dimensionality of the nonlinear search.

Implementations of the subject matter and the functional operations described in this specification, such as various modules, can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is:

1. A method for using magnetic resonance imaging (MRI) to characterize fat, comprising:
    acquiring a magnetic resonance (MR) image that includes MR data from a target;
    determining fat characterization parameters based on the acquired MR data, wherein the fat characterization parameters include an amount of fat, an amount of water, an initial phase, a field inhomogeneity, a T2*, and at least one fat spectrum parameter, and wherein the at least one fat spectrum parameter includes a number of double bonds (NDB), a number of double-double bonds (NDDB), or a chain length (CL) of fat from the target in the MR data; and
    using the determined fat characterization parameters to produce a relationship between regions of fat, regions of water, or regions of fat and water in the MR image,
    wherein the determining fat characterization parameters comprises:
        selecting initial values of the fat characterization parameters;
        estimating values of the fat characterization parameters by iteratively minimizing error between the fat characterization parameters and the acquired MR data;
        generating an MR signal by simulation using the estimated values of the fat characterization parameters; and
        matching the simulated MR signal with an actual MR signal based on the acquired MR data,
    wherein the determining the fat characterization parameters is in accordance with:

$s(t) = [w \cdot \alpha(t) + f \cdot \beta(t)] \cdot \exp(i\phi) \cdot \exp(-R2^* t) \cdot \exp(i\Delta B_0 t)$ $\alpha(t) = a_{water} \cdot \exp(i\omega d_{water} t)$ $\beta(t) = \Sigma a_j(NDB) \cdot \exp(i\omega d_j t),$ where: $a_{water}$ represents the number of protons in water, $a_j$ represents the number of protons in fat, $d_{water}$ represents chemical shifts in water, $d_j$ represents chemical shifts in fat, $\Delta B_0$ represents the field inhomogeneity, R2* represents transverse decay (T2*), $\phi$ represents the initial phase, w represents the amount of water, and f represents the amount of fat.

2. The method of claim 1, wherein the CL is determined from NDB by a linear approximation.

3. The method of claim 2, wherein the linear approximation is substantially CL=16.8+0.24·NDB.

4. The method of claim 1, wherein the NDDB is determined from NDB by a non-linear approximation.

5. The method of claim 4, wherein the non-linear approximation is substantially NDDB=0.092·NDB$^2$.

6. The method of claim 1, wherein the amount of water and the amount of fat are estimated by selecting an initial phase of water and an initial phase of fat to be equal at an echo-time of zero.

7. The method of claim 1, wherein the relationship further includes regions of triglycerides.

8. The method of claim 1, wherein the relationship further includes a number of double bonds.

9. The method of claim 1, wherein the determined fat characterization parameters describe a composition of fat in the target.

10. The method of claim 9, wherein the composition of fat comprises at least six known peak areas, whereby peak area 1 and peak area 2 are determined based on the peak area 3, the peak area 4, the peak area 5, and the peak area 6.

11. The method of claim 1, further comprising:
using the relationship to characterize at least one of a composition of fat, a quantity of fat, a localization of fat, or a change in spatial distribution of fat.

12. The method of claim 1, wherein the target includes a human subject.

13. An MRI system to characterize fat, comprising:
an MRI machine that acquires at least one MR image from a target; and
a processing unit configured to:
command the MRI machine to acquire at least one MR image that includes MR data from the target;
determine fat characterization parameters based on the acquired MR data by:
selecting initial values of the fat characterization parameters,
estimating values of the fat characterization parameters by iteratively minimizing error between the fat characterization parameters and the acquired MR data,
generating an MR signal by simulation using the estimated values of the fat characterization parameters, and
matching the simulated MR signal with an actual MR signal based on the acquired MR data; and
use the determined fat characterization parameters to produce a relationship between regions of fat, regions of water, or regions of fat and water in the MR image,
wherein the fat characterization parameters include an amount of fat, an amount of water, an initial phase, a field inhomogeneity, a T2*, and at least one fat spectrum parameter, and wherein the at least one fat spectrum parameter includes a number of double bonds (NDB), a number of double-double bonds (NDDB), or a chain length (CL) of fat from the target in the MR data;
wherein the determining the fat characterization parameters is in accordance with:

$$s(t)=[w \cdot \alpha(t)+f \cdot \beta(t)] \cdot \exp(i\phi) \cdot \exp(-R2^* t) \cdot \exp(i\Delta B_0 t)$$

$$\alpha(t)=a_{water} \cdot \exp(i\omega d_{water} t)$$

$$\beta(t)=\Sigma a_j(NDB) \cdot \exp(i\omega d_j t),$$

where: $a_{water}$ represents the number of protons in water, $a_j$ represents the number of protons in fat, $d_{water}$ represents chemical shifts in water, $d_j$ represents chemical shifts in fat, $\Delta B_0$ represents the field inhomogeneity, R2* represents transverse decay (T2*), $\phi$ represents the initial phase, w represents the amount of water, and f represents the amount of fat.

14. The MRI system of claim 13, wherein the processing unit is configured to use the relationship to characterize at least one of a composition of fat, a quantity of fat, a localization of fat, or a change in spatial distribution of fat.

15. The MRI system of claim 13, wherein the CL is determined from NDB by a linear approximation, wherein the linear approximation is substantially CL=16.8+0.24·NDB.

16. The MRI system of claim 13, wherein the NDDB is determined from NDB by a non-linear approximation, wherein the non-linear approximation is substantially NDDB=0.092·NDB$^2$.

17. The MRI system of claim 13, wherein the target includes a human subject.

18. A computer program product comprising a nonvolatile computer-readable storage medium having instructions stored thereon, the instructions comprising:
code for acquiring an MR image that includes MR data from a target;
code for determining fat characterization parameters based on the acquired MR data, wherein the fat characterization parameters include an amount of fat, an amount of water, an initial phase, a field inhomogeneity, a T2*, and at least one fat spectrum parameter, and wherein the at least one fat spectrum parameter includes a number of double bonds (NDB), a number of double-double bonds (NDDB), or a chain length (CL) of fat from the target in the MR data; and
code for using the determined fat characterization parameters to produce a relationship between regions of fat, regions of water, or regions of fat and water in the MR image,
wherein the code for determining fat characterization parameters comprises:
code for selecting initial values of the fat characterization parameters,
code for estimating values of the fat characterization parameters by iteratively minimizing error between the fat characterization parameters and the acquired MR data,
code for generating an MR signal by simulation using the estimated values of the fat characterization parameters, and
code for matching the simulated MR signal with an actual MR signal based on the acquired MR data,
wherein the determining the fat characterization parameters is in accordance with:

$$s(t)=[w \cdot \alpha(t)+f \cdot \beta(t)] \cdot \exp(i\phi) \cdot \exp(-R2^* t) \cdot \exp(i\Delta B_0 t)$$

$$\alpha(t)=a_{water} \cdot \exp(i\omega d_{water} t)$$

$$\beta(t)=\Sigma a_j(NDB) \cdot \exp(i\omega d_j t),$$

where: $a_{water}$ represents the number of protons in water, $a_j$ represents the number of protons in fat, $d_{water}$ represents chemical shifts in water, $d_j$ represents chemical shifts in fat, $\Delta B_0$ represents the field inhomogeneity, R2* represents transverse decay (T2*), $\phi$ represents the initial phase, w represents the amount of water, and f represents the amount of fat.

19. The computer program product of claim 18, further comprising code for using the relationship to characterize at least one of a composition of fat, a quantity of fat, a localization of fat, or a change in spatial distribution of fat.

20. The computer program product of claim 18, wherein the CL is determined from NDB by a linear approximation, wherein the linear approximation is substantially CL=16.8+0.24·NDB.

21. The computer program product of claim 18, wherein the NDDB is determined from NDB by a non-linear approximation, wherein the non-linear approximation is substantially NDDB=0.092·NDB².

22. The computer program product of claim 18, wherein the target includes a human subject.

23. An MRI method, comprising:
modeling a MRI-generated fat spectrum from an MR image of a target using at least one of three parameters including a CL, an NDB, or an NDDB, including:
determining fat characterization parameters based on the MR image, wherein the fat characterization parameters include an amount of fat, an amount of water, an initial phase, a field inhomogeneity, a T2*, and at least one fat spectrum parameter, and wherein the at least one fat spectrum parameter includes a number of double bonds (NDB), a number of double-double bonds (NDDB), or a chain length (CL) of fat from the target in the MR data; and
using the determined fat characterization parameters to produce a relationship between regions of fat, regions of water, or regions of fat and water in the MR image,
wherein the determining fat characterization parameters comprises:
selecting initial values of the fat characterization parameters;
estimating values of the fat characterization parameters by iteratively minimizing error between the fat characterization parameters and the acquired MR data;
generating an MR signal by simulation using the estimated values of the fat characterization parameters; and
matching the simulated MR signal with an actual MR signal based on the acquired MR data,
wherein the determining the fat characterization parameters is in accordance with:

$$s(t)=[w \cdot \alpha(t)+f \cdot \beta(t)] \cdot \exp(i\phi) \cdot \exp(-R2^*t) \cdot \exp(i\Delta B_0 t)$$

$$\alpha(t)=a_{water} \cdot \exp(i\omega d_{water}t)$$

$$\beta(t)=\Sigma a_j(NDB) \cdot \exp(i\omega d_j t),$$

where: $a_{water}$ represents the number of protons in water, $a_j$ represents the number of protons in fat, $d_{water}$ represents chemical shifts in water, $d_j$ represents chemical shifts in fat, $\Delta B_0$ represents the field inhomogeneity, R2* represents transverse decay (T2*), $\phi$ represents the initial phase, w represents the amount of water, and f represents the amount of fat.

24. The method of claim 23, wherein the modeling comprises measuring a number of double bonds based on the MR image.

25. The method of claim 23, further comprising:
using the relationship to characterize at least one of a composition of fat, a quantity of fat, a localization of fat, or a change in spatial distribution of fat.

* * * * *